United States Patent [19]
Litts et al.

[11] Patent Number: 5,139,954
[45] Date of Patent: Aug. 18, 1992

[54] DNA PROMOTER FRAGMENTS FROM WHEAT

[75] Inventors: James C. Litts, Davis, Calif.; William R. Marcotte, Jr.; Ralph S. Quatrano, both of Wilmington, Del.

[73] Assignees: E. I. Du Pont de Nemours and Company, Wilmington, Del.; Oregon State University, Corvallis, Oreg.

[21] Appl. No.: 525,060

[22] Filed: May 18, 1990

Related U.S. Application Data

[63] Continuation of Ser. No. 247,188, Sep. 21, 1988, abandoned, which is a continuation-in-part of Ser. No. 174,744, Mar. 29, 1988, abandoned.

[51] Int. Cl.$^5$ .................. C12N 15/11; C12N 15/82; C12N 5/04
[52] U.S. Cl. ................................. 435/320.1; 536/27; 435/240.4; 935/35; 935/36; 935/67
[58] Field of Search ............... 435/172.1, 172.3, 320.1, 435/240.4; 536/27; 935/35, 41, 43, 64, 67; 800/205

[56] References Cited

U.S. PATENT DOCUMENTS 4,579,821 4/1986 Palmiter et al. ................... 435/172.3
4,703,005 10/1987 Nakata et al. ........................ 435/68

OTHER PUBLICATIONS

Kuhlemeier et al., *Ann. Rev. Pl. Physiol.*, 38:221–257 (1987).
Davies, P. (Ed.) *Plant Hormones and Their Roles in Plant Growth and Development*, Martinus Nijhoff Publ. (1987).
Hooft Vanhuijsduijnen et al., *J. Gen. Virol.*, 67: 2135–2143 (1986).
Addicott, *Abscisic Acid*, Praeger Publ., N.Y. (1983).
Zeevaart et al., *Ann. Rev. Plant Physiol.*, 39: 439–473 (1988).
Walton, *Abscisic Acid* (Ed. Addicott), Chapt. 4, pp. 113–146 (1983).
Quatrano, *Oxford Surveys Pl. Mol. Cell. Biol.*, 3: 467–477 (1986).
Bray et al., *Planta*, 172: 364–370 (1987).
Barker et al., *Proc. Natl. Acad. Sci. (USA)*, 85: 458–462 (1988).
Gomez et al., *Nature* 334: 262–264 (1988).
Mundy et al., *EMBO Journal*, 7: 2279–2286 (1988).
Chen et al., *Proc. Natl. Acad. Sci. (USA)*, 83: 8560–8564 (1986).
Chen et al., *EMBO Journal*, 7: 297–302 (1988).
Ebert et al., *Proc. Natl. Acad. Sci. (USA)*, 84: 5745–5749 (1987).
Howard et al., *Planta*, 170: 535–540 (1987).
Lee et al., *Plant Physiology* 85: 327–330 (1987).
Walker et al., *Proc. Natl. Acad. Sci. (USA)*, 84: 6624–6628 (1987).
Ellis et al., *EMBO Journal*, 6: 11–16 (1987).
Williamson et al., *Plant Physiol.*, 86: 208–215 (1988).
Fromm et al., *Proc. Natl. Acad. Sci. (USA)*, 82: 5824–5828 (1985).
Llewellyn et al., *J. Mol. Biol.*, 195: 115–123, (1987).

*Primary Examiner*—David T. Fox
*Assistant Examiner*—Che Chereskin

[57] ABSTRACT

The preparation and use of nucleic acid promoter fragments homologous to the Em gene of wheat to bring the expression of selected genes in plants under external control are described. The Em promoter fragment is responsive to abscisic acid (ABA) and other compounds possessing ABA-like activity. Through transformation of protoplasts and plant cells with recombinant DNA constructs incorporating such promoter fragments, operably linked selected genes are expressed in response to ABA and compounds possessing ABA-like activity. The application of such promoter fragments and constructs to transient assay systems to predict the likelihood of stable transformation in plants is disclosed.

11 Claims, 15 Drawing Sheets

```
  1  AGATCTAAAC TAACACGTGT CCTTACAAAA AATTAAGTGA AATAGAAAAC
 51  ACATAGAATA TAGATATAAA CTAGCAAAAG AGCCCGTGCG TTGCAACGGG
101  AGAATAAATA ATACATGTTC TTAACCCAAT AACCATGACT CAAGACCCTA
151  ATGTGTTCAC GTCCTTTATT TTCACATGGC ATCACATTTG TGTTGTTGAT
201  GGTGGTCTCA GTGCTCACAT AAAGAAAGCG TGTTTGAATG CGGTCAGTTC
251  TAAGGCATCT CTCTCGCGCA CACTCGCTCG AAATAAAATA AGAAATATGT
301  TCTTTTTTCC CGCGAGGTTT TTCACAGGTG TGCATGCGTG GTTATTGATG
351  TTTTCTTTCC ACTCTATCAG TAAAAAAGAA AAACAGATCA TACATTATAG
401  ATTAAGTTCA CACAAAATAA TATTTAGAA ATATTAAAC GCTAAAATA
451  GCATCATATT TAGATTCTAC ACATTTTCT AATCAAGTTT CATATATAAC
501  ATGTTAAAAT TGGAATTACG GTTAAAAGA TATTGATAAT TTTGTTTAGA
551  TAAACTGTCA GTGGGTTTTG TGTTAAACG AAAAAACGA TTCGGTTGAC
601  TTAAGTATGG ACAGTGGGTT GATTAAAACA TCAGAGGGTT TTGCGAGAAA
```

FIG. 3

```
 651  ATGCAAATAA AAGGTTCGGG AGTGAGTTAA ACGGGTACCA CCGCAGTTTA
 701  TTTACGAAAA ATAGAGGGTT TTTTAAAAA  AAATATATGA CGGGCGACCA
 751  GAAACCCAAT TTGCTTTATT ATTATTAAAA AATAAATAA  AATAGTAAAA
 801  ATAAAGATAA AAATAAAAAT ATAATAAAAT GGCTGCATGC ATCTCCGACG
 851  CAGAGGCCGG GGTCATCTTT TAAAAAGAA  GAAATATAAA TATATTAGAG
 901  CAAACCATAC GAAGAAATGG CATGACGATC GGTTCACGGC CAGTCTCCGA
 951  TCGAGCCCGG CCGCTACAAA CGTACACGCG TCGACAATGC ATGCATGCAA
1001  GCAGAGTCTT GAGCTTCTCG TCCCCTTCCT CGGATAACTC CATGCCTTGC
1051  GAGGGCACGC CCATTACGTG TTGTCTTCCA GGCCCTTGCC GGACACGTGG
1101  CGCGACAGCA GGGACAACGA GCAGGCCGAC GCACGTCCGC GTCGCTGCAC
1151  ACGTGCCGCC TCCGTGCTTC ACGACGCACC GCGCCCCTCC AGCTATAAAA
1201  ACACGGCGTA TGGCTCGTCT TCTCCACCAT CGATCATTGG CTCGAGCTCG
1251  AGCGCCAGCA GTTGCATACA CCACACACGC ATCCACACGT CCGTTTCAGG
1301  AACCTTAGCG GTCGAGCACC TGTTAGCAAT GGCG
```

F I G. 3 (Cont.)

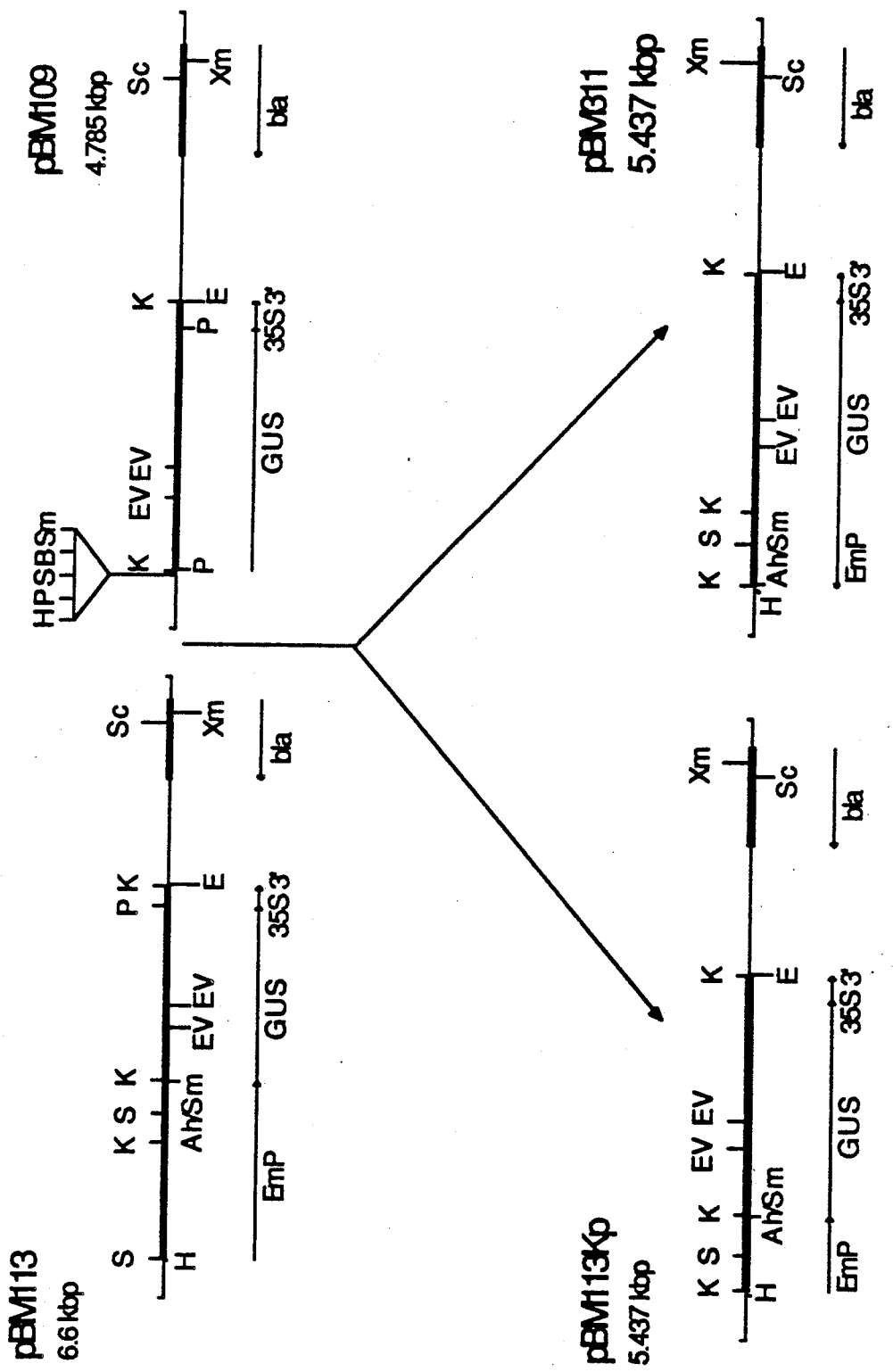
F I G. 5

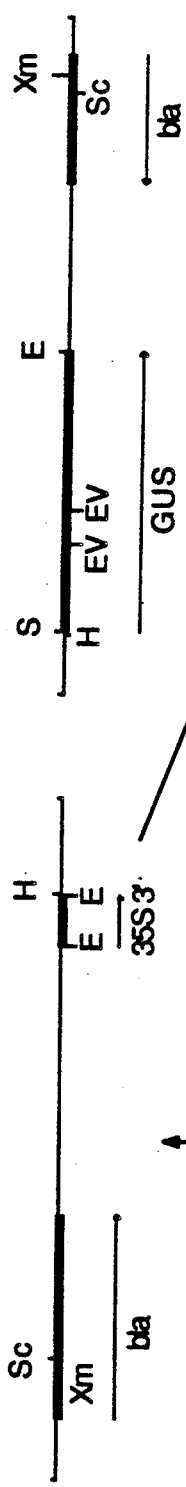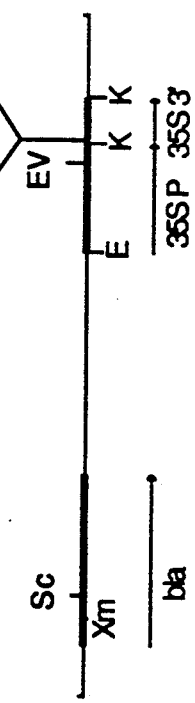
F I G. 9

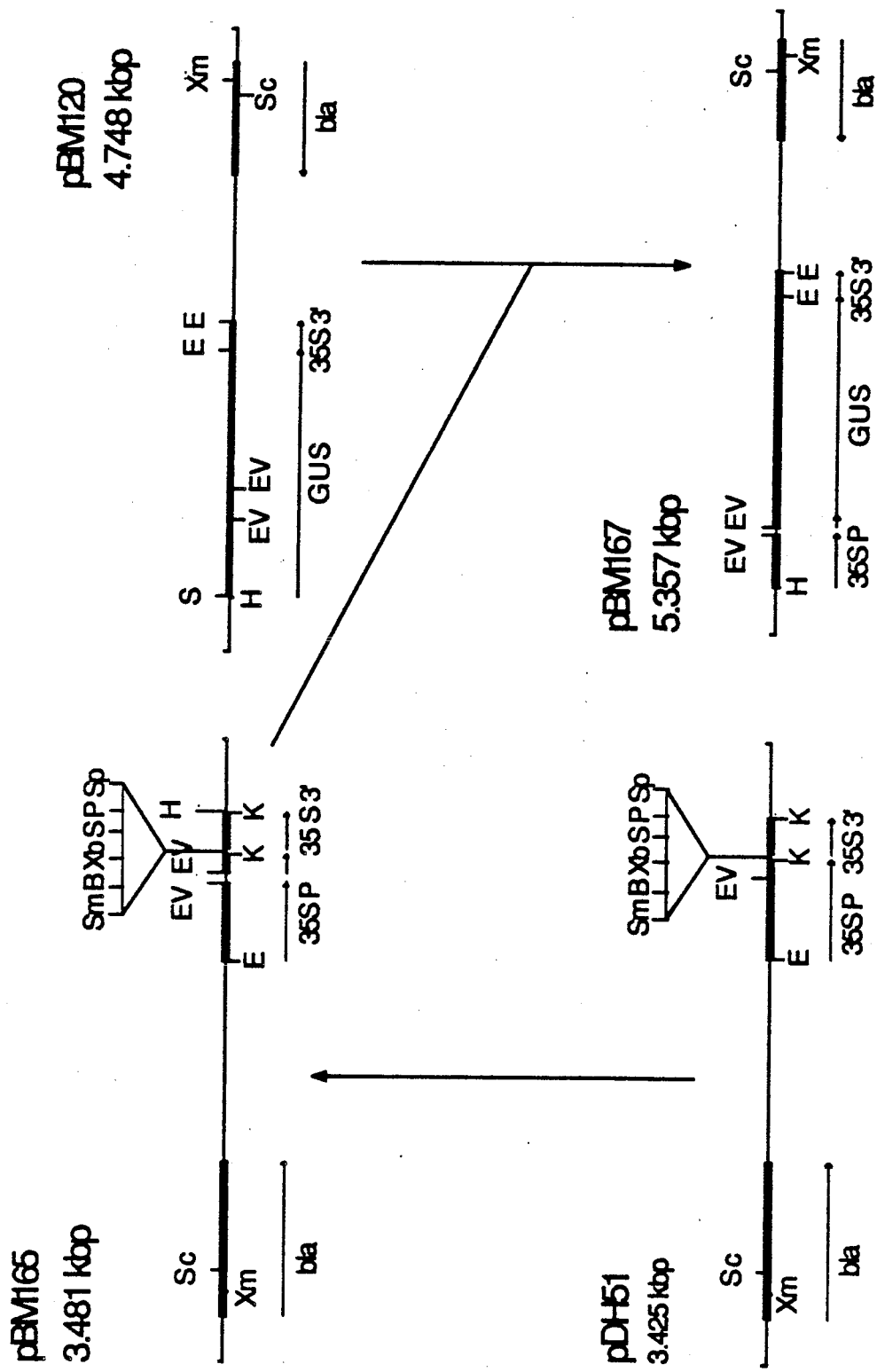
F I G. 10

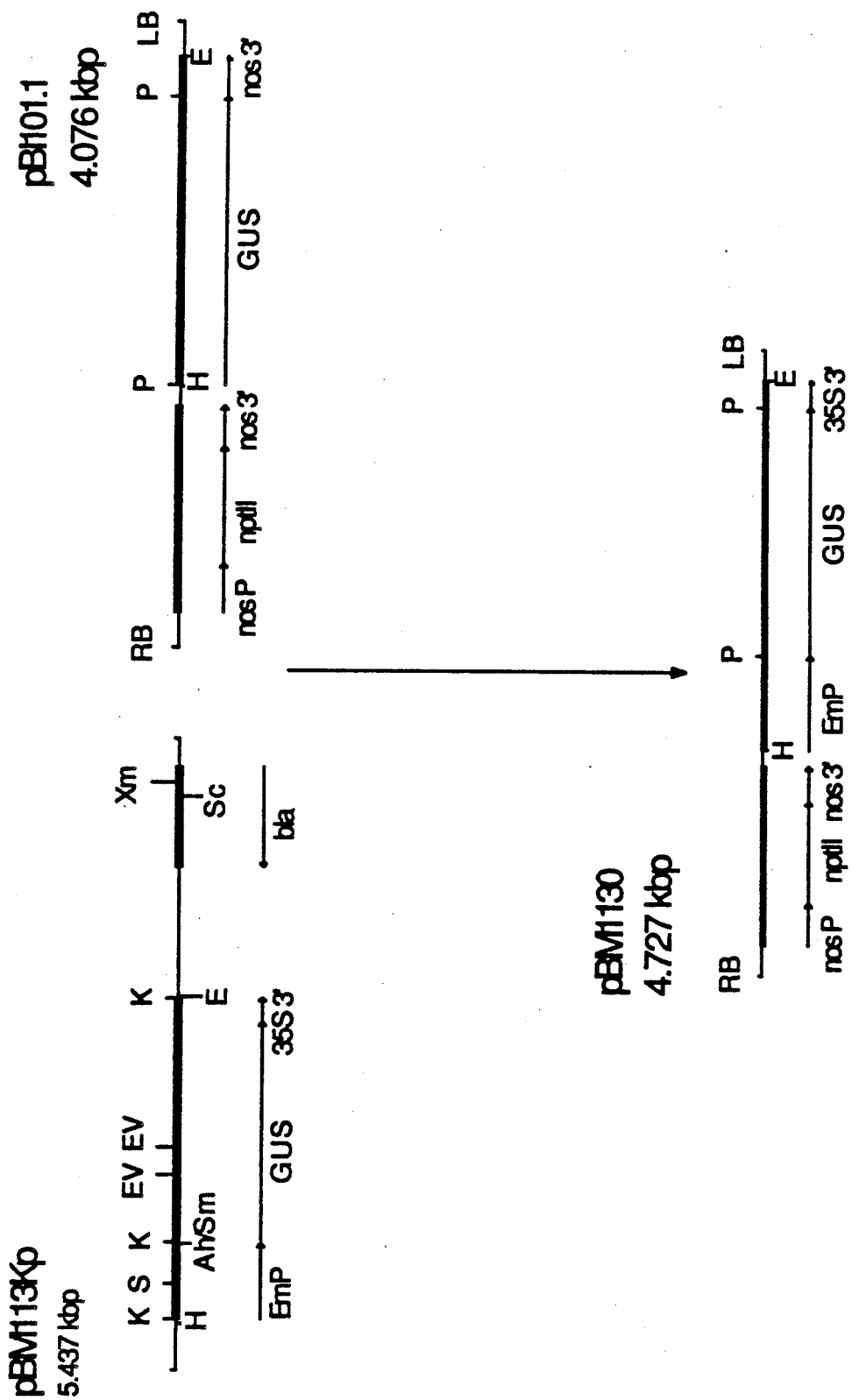
F I G. 13

DNA PROMOTER FRAGMENTS FROM WHEAT

RELATED APPLICATION

This application is a continuation of my copending application U.S. Ser. No. 07/247,188, filed Sep. 21, 1988, now abandoned, which is a continuation-in-part of copending application U.S. Ser. No. 07/174,744 filed Mar. 29, 1988, now abandoned.

FIELD OF THE INVENTION

This invention relates to the preparation of nucleic acid promoter fragments homologous to the Em gene of wheat which are responsive to compounds possessing abscisic acid-like activity, and their incorporation into recombinant DNA constructs to bring the expression of nucleic acid sequences for selected gene products operably linked to the promoter fragments under external control in protoplasts and plants.

BACKGROUND OF THE INVENTION

The external control of the expression of selected gene products in plants through the application of chemical substances can provide important agronomic and foodstuff benefits. The ability to externally control the expression of introduced genes in transgenic plants could be used to (1) prolong or extend the accumulation of desirable nutritional food reserve in seeds, roots, or tubers, (2) produce and accumulate products in plant tissues that are convenient for harvest and isolation, and (3) initiate expression of a toxin at the site of pathogen attack, possibly avoiding contamination of the ultimate food product with the toxin. These and other benefits have been unattainable in the field since means to bring known plant genes under external control in the field have not been available.

While technology exists to transform plants with the genes for selected products, their expression is either continuous throughout the lift cycle (controlled by a constitutive promoter), or is regulated by the developmentally timed program of maturation inherent in each organ/tissue/cell (stage or tissue specific promoters). Continuous expression precludes production at particular stages, in specific tissues or in response to environmentally unpredictable events. Such expression could place a major penalty on yield, due to greatly increased energy demands accompanying prolonged synthesis of the product. Tissue or stage specific expression, although valuable for the temporal and spatial accumulation of products, is under the variable timing of the developmental program of the plant. Precise developmental control of gene expression would necessitate the isolation of a multitude of stage and tissue specific promoters in all crop plants of interest. It wold be desirable to externally control the expression of an introduced gene product by the application of a specific chemical which can induce a specific promoter to activate the accumulation of a desired gene product. Hence, one chemical/promoter combination can be interactive at any stage or in any tissue available to the chemical, throughout the life cycle of any one of a large number of transformable plants, to control any desired gene product.

Certain genes can be induced by environmental factors such as light, heat shock and anaerobiosis. The promoters of these inducible genes from plants have been extensively analyzed (c.f., Kuhlemeier et al., *Ann. Rev. Pl. Physiol.*, 38:221-257 (1987)). However, the inducers of these genes (i.e., light, temperature and $O_2$ levels) are not easily or practically controllable under normal agronomic techniques.

Numerous chemicals, both natural and synthetic, have been shown to affect the growth and development of plants. A number of these plant growth regulators occur naturally, such as the hormones auxin, gibberellic acid, cytokinins, ethylene and abscisic acid (c.f., Davies, P. (Ed.) *Plant Hormones and Their Roles In Plant Growth and Development*, Martinus Nijhoff Publ. (1987)), while others have equally dramatic effects such as salicylic acid (Hooft Vanhuijsduijnen et al., *J. Gen. Virol.*, 67:235-2143 (1986)). When these growth regulators are applied to various plant cells/tissues/organs, a change in the metabolism of the plant is observed which has been shown with each of the above regulators to result from new gene expression. Some products of these genes, as well as some genes themselves, have been isolated and characterized. The instant invention focuses on the phytohormone abscisic acid (ABA), 3-methyl-5-(1'-hydroxy-4'-oxo-2',6',6',-trimethyl-2'-cyclohexene-1'-yl)-cis, trans-2,4-pentadienoic acid (c.f. Addicott, *Abscisic Acid*, Praeger Publ., N.Y. pp. 607 (1983)). ABA is involved in numerous processes such as stomatal closure, bud/seed dormancy, inhibition of seed germination, as well as in responses of plants to physical perturbations or stresses such as temperature and water (c.f. Zeevaart and Creelman, *Ann. Rev. Plant Physiol.*, 39:439-473 (1988)). Numerous compounds have been described that mimic ABA in these physiological process, i.e., they are ABA-like (c.f. Walton, In *Abscisic Acid* (Ed. Addicott), Chapt. 4, pp. 113-146 (1983)). Our immediate interest focuses on the involvement of ABA in two of these key plant processes; accumulation of storage reserves in seeds and the response of plants to water stress (drought).

During seed formation in a wide variety of seeds, the endogenous ABA level increases dramatically, as it does in water-stressed tissue. Genes from the seeds of six plants (cotton, soybean, rice, maize, wheat and rapeseed) have been isolated that respond to ABA (when tissue is treated in vitro with the phytohormone) by accumulating the products of these same genes. The response is an increase in the mRNA levels of these specific genes (c.f., Quatrano, *Oxford Surveys Pl. Mo. Cell. Biol.*, 3:467-477 (1986)). Although the characterization of some of these genes has been extensive, only in the case of the β-conglycinin gene from soybean has an ABA-regulated gene been expressed in a transgenic plant; in petunia and tobacco by Bray et al., *Planta* 172:364-370 (1987) and in tobacco by Barker et al., *Proc. Natl. Acad. Sci.* (USA) 85:458-462 (1988).

The goal in each case is to identify the DNA sequences that control the expression of these genes in a tissue-specific, stage-specific and environmentally regulated manner. Bray et al. demonstrated this specific regulation in transgenic plants when a 4.2 kilobase (kb) fragment of the natural gene was transferred. In addition to the coding region, it contained a 1.1 kb 5' fragment and a 1.3 kb 3' fragment. Barker et al. transferred to tobacco a much larger fragment (12.3 kb) that contained more genes that the β-conglycinin gene. Neither group characterized further, which part(s) of these large fragments might be responsible for the specific ABA induction effect, nor did they report treating transformed tissue with ABA to determine if the foreign gene would responsive to hormone addition.

Gomez et al., *Nature* 334:262-264 (1988), reported that when immature maize embryos, like wheat, are cultured in the presence of ABA they express a new set of genes in response to the hormone. One ABA-regulated gene (pMAH9), isolated in this report, codes for a 15.4 Kd protein. The mRNA for this protein is also expressed when mature leaf tissue is wounded or water stressed. The complete sequence of the coding region and parts of the 3' and 5' flanking regions are given, but no information is reported as to the sequence within the promoter region which is essentially for ABA regulation.

Mundy and Chua, *EMBO Journal*, 7:2279-2286 (1988), characterized the full genomic sequence of a gene from rice (RAB 21) which is induced by ABA, as well as by salt (NaCl), and water stress in numerous tissues, e.g., roots, leaves, embryos, suspension cultures. Although the complete sequence of the coding region (approximately 1 kb) and the 5' regulatory or promoter region (approximately 1.5 kb) is given, no information is reported as to the sequences within the promoter region which are essential for ABA regulation of the coding sequences. There is no teaching regarding the isolation of a promoter fragment, or its potential utility to achieve external control of plant gene expression. The authors themselves (p. 2285) state that "the regulatory roles of these different GC-rich repeats remains to be established. ..." Applicant's invention lies in the isolation of promoter fragments, their use in constructs to transform protoplasts and plants, and in achieving the external control of plant gene expression.

Other seed-specific genes that have not been shown to be regulated by ABA, or by any other hormone, have been analyzed in the same manner. For examples, Chen et al., *Proc. Natl. Acad. Sci.* (USA) 83:8560-8564 (1986) showed that the region between −159 and −257 base pairs (bp) 5' to the transcription start site of the α-conglycinin gene is the required region for seed specificity. More recently, Chen et al., *EMBO Journal*, 7:297-302 (1988), constructed a chimeric gene comprising a 170 bp fragment from the α-conglycinin promoter region (−78 to −257) in different positions and orientations to the constitutive viral 35S promoter linked to the reporter gene chloramphenical acetyl transferase (CAT). They showed that the 170 bp 5' fragment enhances expression of the CAT gene in a tissue-specific and temporally regulated manner.

However, delineation of the specific regulatory regions required these investigators to assay for expression in transgenic plants at the stage of seed formation. This required long periods of time until the plants flowered and set seed (several months). Transient assays for promoter analysis have been reported and represent a faster way to delineate those promoter fragments that are regulatory. However, none of these reports which follow involve the use of a chemical inducer.

Ebert et al., *Proc. Natl. Acad. Sci.* (USA) 84:5745-5749 (1987), disclose studies of the active fragment of DNA constituting the nopaline synthase promoter. This promoter is constitutive rather than inducible, and while of bacterial origin, operates in a wide range of plant tissues. A construction was made such that the promoter controlled the expression of the reporter gene CAT. The authors reported that a fragment of 33 bp (−97 to −130) of DNA was necessary to promote expression of the CAT gene. They reported further that the presence of two copies of the fragment tripled the expression of the CAT gene. These results from stably transformed tobacco tissue were repeatable in a transient assay using tobacco protoplasts. Comparison of the level of CAT gene expression controlled by the fragments in both the transient expression of tobacco protoplasts and stably transformed tissues resulted in some differences. The authors nevertheless indicated their belief that such transient assays are valuable for "the study of upstream elements and trans-acting factors".

Howard et al., *Planta*, 170:535-540 (1987), studied the anaerobic induction of the maize alcohol dehydrogenase (Adh1) gene by electroporating gene fragments of Adh1 into maize protoplasts from suspension culture cells, subjecting these protoplasts to reduced oxygen levels and assaying for Adh1 expression 20 hours later. To facilitate measurement of Adh1 gene expression regulated by anaerobiosis, they fused the 5' promoter or regulatory fragment of the native Adh1 gene (1096 base pairs) to CAT. Their results demonstrated the normal regulation of an inducible promoter from a monocot maize gene (i.e., Adh1) when electroporated into protoplasts derived from a homologous cell culture system. They showed that just the Adh1 promoter fragment, without the coding and 3' regions of the Adh1 gene, is sufficient for anaerobic induction of the CAT gene.

Lee et al., *Plant Physiology* 85:327-330 (1987), have reported further definition of the size of the DNA fragment responsible for anaerobic induction of the maize Adh1 gene. Utilizing a plasmid vector that facilitated placement of any desired gene adjacent and 3' to the promoter, they inserted the gene for CAT next to the Adh1 gene. Using this plasmid, they transformed maize protoplasts and measured the production of CAT 24 hours later. By altering the size of the promoter DNA sequences in the construction, Lee et al. determined that 146 bp 5' to the transcription start site were sufficient to place the production of CAT under anaerobic induction. However, the expression of CAT was increased 5× or 8× by the addition of 266 or 955 bp, respectively, of contiguous 5' promoter sequences.

Walker et al., *Proc. Natl. Acad. Sci* (USA) 84:6624-6628 (1987), continued the studies of the DNA sequences of the 5' promoter region of the maize Adh1 gene required for gene expression induced by anaerobic conditions in a transient assay. They determined that control of anaerobic induction of gene expression resided in two sequences from the promoter: those being the sequence between −133 and −124 bp and the sequence between −113 and −99 bp (5' to the transcription start site). Both sequences are necessary. Attachment of this 40 bp element to an unrelated viral promoter confers anaerobic regulation.

Ellis et al., *EMBO Journal* 6:11-16 (1987), indicate that when the fragment of DNA between base pairs −1094 and +106 bp of the maize Adh1 gene was placed next to the sequence of DNA encoding CAT and the construction was stably transformed into tobacco cells, only extremely low levels of CAT gene expression could be observed under appropriate anaerobic conditions. In fact, only CAT messenger RNA was detected. However, promoter elements from the octopine synthase gene of bacteria, or those from the Cauliflower Mosaic Virus (CaMV), linked 5' to the Adh1 promoter, stimulated the expression of the CAT gene and permitted detection of CAT after anaerobic induction. The fragment of DNA, consisting of 247 bp adjacent and 5' to the transcription start site of the structural gene for Adh1, was sufficient to put the expression of the CAT gene under anaerobic control. Therefore, anaerobic control by the 247 bp fragment of DNA was maintained even when the octopine synthase and CaMV 35S promoters, which are constitutive promoters, were present. The region of the Adh1 promoter responsible for anaerobic induction demonstrated in transient assays by Howard et al., Lee et al., and Walker et al. were similar to the region showing anaerobic induction in stably transformed plants by Ellis et al.

Patents have been issued to animal and microbial systems in which selected gene sequences have been induced by chemicals in the environment that interact with certain regulatory sequences. U.S. Pat. No. 4,579,821, issued to Palmiter and Brinster, discloses the isolation of promoter/regulator sequences of the mouse metallothionein-I gene and its use to control the expression of selected DNA sequences operably linked to the promoter by exposure to heavy metal ions or steroid hormones. The expression of thymidine kinase fused to the metallothionein-I promoter was obtained in differentiated cells of adult mice upon administration of cadium or dexamethasone. U.S. Pat. No. 4,703,005, issued to Nakata and Shinagaua, discloses the isolation of a gene for phosphate-binding protein (phoS) to which was fused a foreign gene 3' to phoS. The foreign gene is controlled by phosphate in the culture medium.

Despite considerable effort to characterize the molecular basis of the response of plant tissue to hormones, the signal/transduction pathway from chemical to gene is not well understood. While reports of plant promoter sequences stimulated by light and anaerobic stress have appeared, no disclosures of inducible plant promoters responsive to chemical substances which can be applied in the field to control gene expression have appeared. At this time, a clear need exists for promoter sequences and recombinant constructs for the transformation of plants which would enable external control of selected genes which can confer agronomic advantages. Further, this specificity of expression should be amenable to external control through exposure to chemical substances which can be readily manipulated.

SUMMARY OF THE INVENTION

A means to externally control the expression of selected genes in plant cells, plants and protoplasts through exposure to a chemical substance has been discovered. The Em gene of wheat is an inducible gene, responsive to ABA, which is accumulated and implicated in the physiological events of embryo maturation and drought stress protection. Applicants have discovered novel promoter fragments derived from the Em gene which can be used to achieve external control of selected genes, and it is believed that promoter regions from other plant genes homologous to the Em structural gene of wheat will function similarly. Specifically, one preferred aspect of the present invention is a nucleic acid promoter fragment comprising a nucleotide sequence from the 5' flanking promoter region of a plant gene homologous to the Em structural gene of wheat, said promoter fragment being responsive in transformed plant cells to compounds possessing ABA-like activity such that the expression of DNA sequences for selected gene products operably linked on the 3' side of said promoter fragment can be controlled with the proviso that such promoter fragments are not responsive to phaseic acid. Preferred is a nucleic acid promoter fragment comprising a nucleotide sequence from the 5' flanking promoter region of the Em structural gene of wheat, said promoter fragment being responsive in plant cells to compounds possessing ABA-like activity such that the expression of nucleic acid sequences for selected gene products operably linked on the 3' side of said promoter fragment can be controlled. The invention is thus broadly applicable for securing control of many genetic processes, ranging from the alteration of existing regulation of endogenous genes in plant cells, to securing selective regulation of expression of selected foreign genes stably incorporated in plant cells. Preferred compounds possessing ABA-like activity include ABA, Compound C, Compound D, Compound E, and Compound F (as defined herein).

Presently, preferred promoter fragment for use in practice of the invention are derived from the Em gene of wheat, specifically, an 1850 bp nucleic acid promoter fragment. More preferred is a 640 bp nucleic acid promoter fragment. Most preferred, by virtue of ease of use in constructs and effective use in plants, are a 254 bp and a 50 bp nucleic acid promoter fragment derived from the regulatory DNA sequence controlling the expression of the Em structural gene of wheat. Such promoter fragments are also defined by their nucleic acid sequence.

Another aspect of this invention involves a recombinant DNA construct capable of modifying the properties of a protoplast comprising a nucleic acid promoter fragment of the Em gene of wheat, and a DNA sequence for a selected gene product operably linked to said promoter fragment such that upon exposure to a compound possessing ABA-like activity said DNA sequence for a selected gene product is expressed. Another embodiment involves a recombinant DNA construct capable of transforming a plant cell comprising a nucleic acid promoter fragment of the Em gene of wheat, a DNA sequence for a selected gene product operably linked to said promoter fragment, and a suitable regulatory sequence such that upon exposure to a compound possessing ABA-like activity said DNA sequence for a selected gene product is expressed. These constructs may be incorporated into DNA plasmid vectors to provide useful tools in the transformation of a wide variety of plant cells, plant tissues and plants.

Yet another aspect of this invention involves a transient assay method to evaluate the likelihood of expression of a selected gene product in a stably transformed plant comprising the steps of (a) preparing protoplasts from rice, (b) transferring to said protoplasts a recombinant DNA construct incorporating a nucleic acid promoter fragment of the Em gene of wheat and an operably linked DNA sequence for a selected gene product, (c) incubating said protoplasts containing said construct with a compound possessing ABA-like activity, and (d) measuring the amount of said selected gene product expressed in response to said compounds.

Another process embodiment of the invention involves a method for controlling the expression of a selected gene product in a plant comprising the steps of (a) transforming said plant with a recombinant DNA construct incorporating a nucleic acid promoter fragment of the Em gene of wheat and an operably linked DNA sequence for a selected gene product, and a suitable regulatory sequence, (b) exposing said plant to a compound possessing ABA-like activity, and (c) causing said plant to express said selected gene product at a desired time.

A final aspect of the invention involves a nucleic acid fragment for controlling over-production of a selected gene product in plants in response to drought conditions comprising a nucleic acid promoter fragment responsive to ABA inserted into the CaMV 35S promoter sequence. In this embodiment, it is believed that environmental factors leading to increased levels of ABA within the plant will trigger over-production of selected gene products which will protect the plant.

Characterization of the regulation of the promoter fragment of the Em gene of wheat has been carried out utilizing rice protoplasts. This system is preferred base upon the rapid response of transformed rice protoplasts to compounds possessing ABA-like activity, the ability to regenerate transgenic rice plants from protoplasts and to predict the response in a stably transformed plant.

Further, to easily and rapidly measure the response of a compound possessing ABA-like activity, a reporter gene is operably linked to the promoter fragment. The reporter gene chosen is that for the enzyme $\beta$-glucuronidase (GUS) for several reasons; no background enzyme activity is detected in plant cells, an extremely sensitive and quantitative fluorometric assay is available, and the enzyme activity is very stable. A recent review of the merits of using GUS is provided by Jefferson, *Pl. Mol. Biol. Rep.*, 5:387–405 (1988).

BRIEF DESCRIPTION OF THE DRAWINGS

FIG. 3 is the nucleotide sequence of the Em gene 5' flanking region from −1328 to +6 from the translational start codon. The translational start codon, ATG, is underlined.

FIG. 5 is a physical map of plasmids pBM113Kp and pBM311 as derived from plasmids pBM109 and pBM113.

FIG. 9 is a physical map of plasmids pCS102 and pBM120 as derived from plasmids pDH51 and pBM119.

FIG. 10 is a physical map of plasmids series pBM165 and plasmid series pBM167 as derived from plasmids pDH51, a 56 bp oligonucleotide, and plasmid pBM120.

FIG. 13 is a physical map of plasmid pBM1130 as derived from plasmids pBM113Kp and pBI101.1.

DETAILED DESCRIPTION OF THE INVENTION

Figure 1:
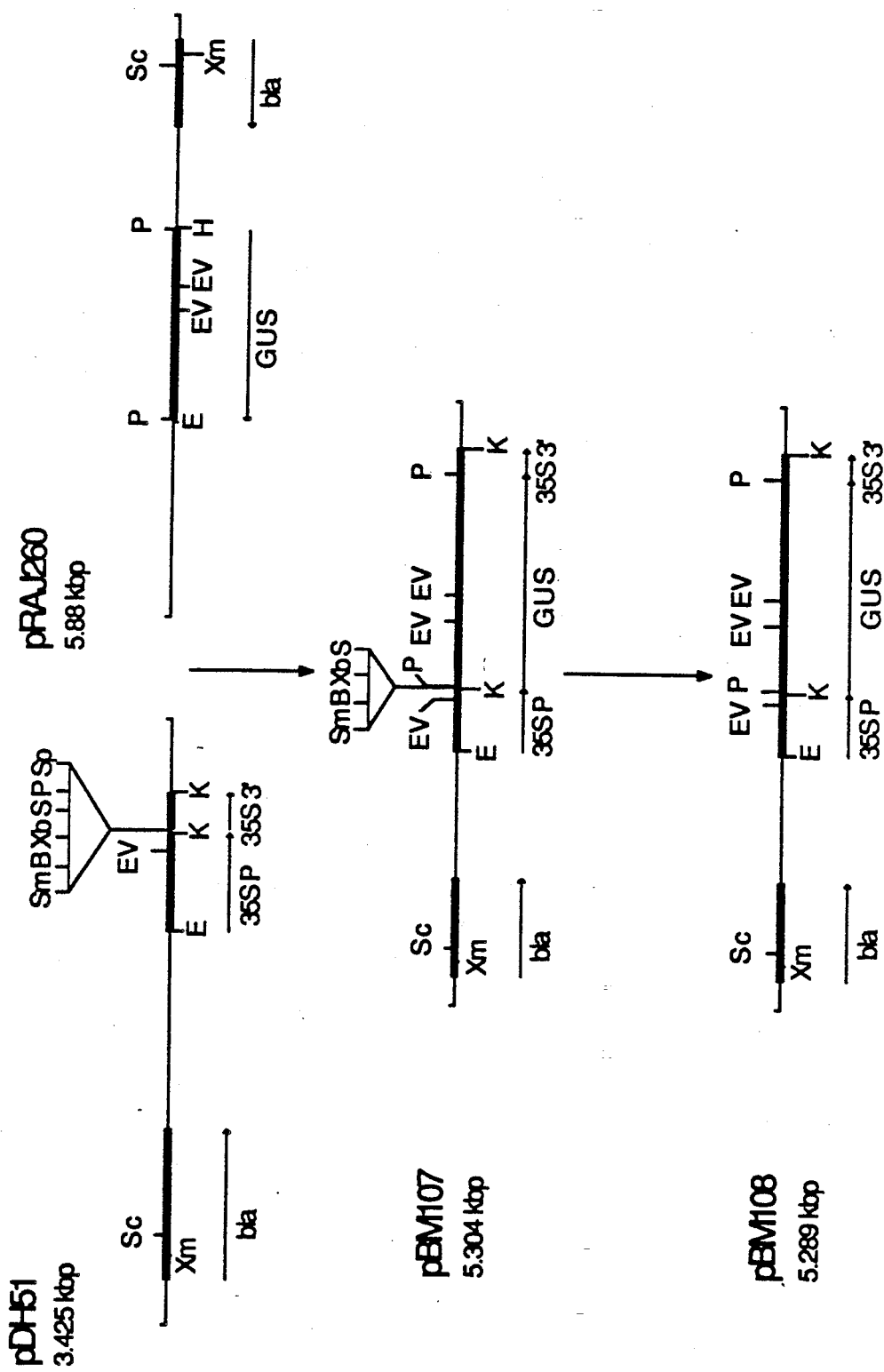
FIG. 1 is a physical map of plasmid pBM108 as derived from plasmids pRAJ260 and pDH51.

The present invention provides nucleic acid promoter fragments of the Em gene of wheat which are responsive to compounds possessing ABA-like activity to bring the expression of DNA sequences for selected gene products under external control. A major storage protein found in mature wheat embryos is synthesized early during the process of seed maturation. Its synthesis can be monitored by the accumulation of a radioactive amino acid $^{35}$S-methionine. Based on these characteristics, Grzelczak et al., *Canad. J. Biochem.* 60:389–397 (1982), named this protein "early-methionine-labelled", or Em. Em begins to accumulate in embryos by 21 days post anthesis, i.e., Stage III. When embryos are removed from the grain at Stage II (15 days) or III and cultured in vitro, they germinate precociously into normal seedlings and Em is not accumulated. Williamson and Quatrano, *Europ. J. Biochem.*, 152:501–507 (1985) showed that if $10^{-6}$ to $10^{-4}$M ABA is present in the culture medium, both the Em mRNA and protein are rapidly synthesized and accumulated. They further studied the regulation of the native Em gene in wheat by application of ABA to intact mature embryos (Williamson and Quatrano, *Plant Physiol.*, 86:208–215 (1988)). Em is one of a family of about 50 proteins that appear to be regulated in this manner by ABA. The Em gene of wheat, encoding the Em protein, includes the coding region for the protein, and all necessary regulatory sequences upstream (5') and downstream (3') and/or within the coding region, such as the upstream (5') promoter region. Another storage protein from wheat embryos, a 7S globulin, is included in this family (Williamson and Quatrano, *Plant Physiol.*, 86:208–215 (1988)). This globulin class of storage proteins has members in the monocot maize (Khavkin et al., *Planta*, 143:11-20 (1978)) and has been extensively studied and characterized in dicot seeds, especially the legumes (Casey et al., Oxford Surveys Pl. Mol. Cell Biol., 3:1–95 (1986)). Based on the distribution of this class of storage proteins in seeds of many plants, we would expect that proteins and genes homologous to Em from wheat would be represented in all seed plants.

In the context of this disclosure, a number of terms shall be utilized. As used herein, the term "promoter region" refers to a sequence of DNA, usually upstream (5') to the coding sequence, which controls the expression of the coding region by providing the recognition for RNA polymerase and/or other factors required for transcription to start at the correct site. A "promoter fragment" constitutes a fraction of the DNA sequence of the promoter region. "Nucleic acid" refers to a large molecule which can be single-stranded or double-stranded, composed of monomers (nucleotides) containing a sugar, phosphate and either a purine or pyrimidine. In higher plants, deoxyribonucleic acid (DNA) is the genetic material while ribonucleic acid (RNA) is involved in the translation of the information in DNA into proteins. The term "nucleotide sequence" refers to a polymer of DNA or RNA which can be single-stranded or double-stranded, optionally containing synthetic, non-natural or altered nucleotide bases capable of incorporation into DNA or RNA polymers. As used herein, "DNA sequences for selected gene products" refers to a gene or DNA sequences that codes for a specific protein. "Regulatory sequence", as used herein, refers to a nucleotide sequence located upstream (5'), within, and/or downstream (3') to a DNA sequence for a selected gene product whose transcription and expression is controlled by the regulatory sequence in conjunction with the protein synthetic apparatus of the cell. The term "recombinant DNA construct" refers to a plasmid, virus, autonomously replicating sequence, phage or nucleotide sequence, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product into a plant cell. As used herein, "monocotyledonous plant" or monocot refers to a plant whose seeds have only one cotyledon, or organ of the embryo which stores and absorbs food. Similarly, "dicotyledonous plant" or dicot, refers to a plant whose seeds have two cotyledons. A "protoplast" refers to a plant cell without a cell wall or extracellular matrix.

As used herein, "transformation" means processes by which cell/tissue/plant acquire properties encoded on a nucleic acid molecule that has been transferred to the cell/tissue/plant. "Transferring" refers to methods to transfer DNA into cells including microinjection, permeabilizing the cell membrane with various physical (e.g., electroporation) or chemical (e.g., polyethylene glycol, PEG) treatments, or by integration into the host nuclear DNA by the bacterial vector *Agrobacterium tumefaciens*. As used herein, "exposing" a protoplast or a plant to a chemical substance refers to treating, incubating, contacting said protoplast or plant with the substance. The term, "operably linked" refers to the chemical fusion of two fragments of DNA in a proper orientation and reading frame to be transcribed into functional RNA. As used herein, the term "homologous to" refers to proteins or nucleic acids having similar sequences of amino acids or nucleotides respectively, i.e., proteins or nucleic acids with the same structural or functional properties. The term "expression", as used herein, is intended to mean the transcription and translation to gene product from a gene coding for the sequence of the gene product. In the expression, a DNA chain coding for the sequence of the gene product is first transcribed to a complementary RNA which is called a messenger RNA and, then, the thus transcribed messenger RNA is translated into the above-mentioned gene product. Expression which is constitutive and further enhanced by an externally controlled promoter fragment thereby producing excess copies of messenger RNA resulting in the accumulation of more than normal quantities of the selected gene product, is referred to as "over-production". The "translation start codon" refers to a unit of three nucleotides (codon) in a nucleic acid that specifies the initiation of the structural gene or protein sequence. "Chemical inducers" are compounds which interact with promoters to trigger the expression of operably-linked structural genes, selected gene products or reporter genes such as GUS.

"ABA-like" compounds are compounds that mimic the effect of ABA in one or more physiological processes or bioassays, such as stomatal closure, bud/seed dormancy, inhibition of seed germination and responses of plants to physical stress (c.f. Addicott, *Abscisic Acid*, Praeger Publ., N.Y. 607 pp. (1983); Addicott and Lyon, *Ann. Rev. Plant Physiol.* 20:139–164 (1969); Zeevaart and Creelman, *Ann. Rev. Plant Physiol.* 39:439–473 (1988)).

"Transformed plant cell(s)" can include a protoplast(s) (plant cell without a cell wall) an isolated cell(s) or a cell(s) within a transformed plant.

The techniques of DNA recombination used throughout this invention are known to those skilled in the art and are generally described in Maniatis et al., *Molecular Cloning: A Laboratory Manual*, Cold Spring Harbor Laboratory, Cold Spring Harbor, N.Y. (1982).

Enzymatic Treatments of DNA

1. Restriction of Enzyme Digestions

The restriction enzyme digestion buffers and digestion conditions used are those supplied by the manufacturer of each particular enzyme. When recommended by the manufacturer, dithiothreitol (DTT) is added from a separate sterile stock solution to the recommended concentration. Enzyme is added to give 5–10 units per microgram of DNA and the reaction mixture is adjusted to the appropriate final volume with $H_2O$ (usually 10–20 $\mu$l). The restriction enzyme reaction mixtures used routinely contained 0.7–2.0 $\mu$g plasmid DNA. The reaction mixtures are mixed by vortexing and then incubated at the appropriate temperature for 1.5 hours. Digestion of DNA with multiple enzymes is done concomitantly when the optimal salt and temperature conditions of the separate enzymes are similar. When these conditions are sufficiently different, digestions are done sequentially beginning with the enzyme requiring the lowest salt concentration. Subsequent reactions are supplemented to the appropriate buffer conditions for the enzyme used.

2. Ligation

For ligation of DNA fragments, T4 DNA ligase from Bethesda Research Laboratories, Gaithersburg, Md. 20877 and the buffer supplied with the enzyme (50 mM Tris/HCl pH 7.6, 10 mM $MgCl_2$, 1 mM ATP, 1 mM DTT, and 5% (w/v) polyethylene glycol (PEG) is used. One to two units of enzyme are added per microgram of DNA. The reaction mixtures are incubated at either 16° C. overnight or at 37° C. for 2–4 hours.

3. Fill-in/Chew-back Reactions

It is necessary, on occasion, to fill-in or chew-back the overhang of a particular restriction site prior to ligation. Fill-in is used for those enzymes that leave a 5' overhang at the site of restriction and chew-back is used for those enzymes that leave a 3' overhang. The fill-in reaction utilizes the Klenow fragment of *E. coli* DNA polymerase I. The reaction mixture is 1 unit of Klenow fragment, 16 $\mu$M of deoxynucleotide triphosphates (dNTPs) (all four) in 10–50 mM Tris/HCl (pH 7.5–8.0), 0–50 mM NaCl and is performed at 37° C. for 15 minutes. When convenient, the reaction is performed in the same tube in which the reaction with the restriction enzyme(s) took place. In those cases, the salt concentration is adjusted to a final concentration of less than 50 mM. When secondary restriction digestion(s) are to be performed, the Klenow fragment is denatured by heating it to 65° C. for 10 minutes to avoid unwanted filling-in of secondary restriction site ends.

T4 DNA polymerase may be used for filling-in restriction sites which leave 5' overhangs and for chewing-back restriction sites which leave 3' overhangs. The reaction mixture for both reactions is 10 units of T4 polymerase, 300 $\mu$M dNTPs (all four), 40 mM Tris/HCl (pH 7.5), 10 mM $MgCl_2$, 5 mM DTT, 50 mM NaCl, 50 $\mu$g/ml bovine serum albumin (BSA) and is performed at 11° C. for 20 minutes. Similarly, when secondary restriction digestions are to be performed, the T4 polymerase is denatured by heating to 75° C. for 10 minutes to avoid unwanted filling-in or chewing-back of secondary restriction site ends.

4. Exonuclease III-Mediated Deletion

This procedure is designed for the construction of fragments of DNA reduced by the progressive, unidirectional deletion of DNA. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series (e.g. Promega-Biotec, Madison, Wis. 53711, Erase-A-Base System, Cat# E5750).

The procedure is performed as follows: The DNA molecule of interest (usually a plasmid) must contain at least two unique restriction sites. One of these sites (the first) will be the one from which the deletion reaction will proceed and may be adjacent to or within the DNA to be deleted. The second site must be in a position such that the first site lies between the second site and the DNA to be deleted. The molecule is cleaved with the restriction enzymes (as described above) to prepare for the deletion reaction. The restriction site from which the deletion is to proceed must produce a 5' protruding end or a blunt end (sensitive to exoIII digestion). The other restriction site must either produce a 4 base 3' protruding end, or must be filled-in with α-phosphorothioate nucleotides (insensitive to exoIII digestion). When one end of the molecule must be protected from exoIII digestion with the α-phosphorothioate nucleotides, the plasmid is digested with this enzyme first. The ends will then be filled-in in the presence of 40 μM each of the four α-phosphorothioate nucleotides, 1 mM DTT, 20 mM Tris/HCl (pH 8.0), 100 mM $MgCl_2$ and 50 units/ml Klenow fragment at 37° C. for 10 minutes.

The sample is then heated to 70° C. to inactivate the Klenow fragment and the second restriction digestion is performed. If the second restriction enzyme is incompatible with the salt concentrations in the Klenow reaction, the sample must first be extracted with an equal volume of phenol:$CHCl_3$:isoamyl alcohol (25:24:1), and the DNA isolated by precipitation from the aqueous phase by the addition of 2 volumes of ethanol. After the second restriction digestion is finished, the sample is extracted and the DNA again precipitated by addition of ethanol.

The exoIII digestion may now be performed on the isolated DNA. The procedure outlined below is adapted for digesting approximately 5 μg of double-cut plasmid DNA and taking samples at 25 intervals of time: The DNA sample is dissolved in 60 μl of 1×exoIII buffer (66 mM Tris/HCl (pH 8.0), 6.6 mM $MgCl_2$) and 250-500 units of exoIII nuclease is added, mixed rapidly and the sample is incubated at 37° C. Aliquots (2.5 μl) are removed at various times from the reaction tube and added to 7.5 μl aliquots of S1 nuclease mix and kept on ice. S1 nuclease mix consists of 40 mM potassium acetate (pH 4.6), 0.33 mM NaCl, 1.35 mM $ZnCl_2$, 6.67 mM glycerol containing 0.3 units of S1 nuclease/μl. After all the samples are taken, the S1 mix tubes containing the aliquots of the different time intervals are removed from the ice and incubated at room temperature for 30 minutes. To stop the S1 reaction, 1 μl of S1 stop buffer (0.3M Tris base, 50 mM ethylenediaminetetraacetic acid (EDTA) is added and the samples are heated to 70° C. for 10 minutes.

Aliquots (2 μl) are removed from the sample tubes and are analyzed on a 1% agarose gel to determine the extent of digestion. The remainder of each of the samples are transferred to 37° C. and 1 μl of Klenow mix (1×Klenow buffer-see above containing 0.10-0.15 unit Klenow fragment/μl) is added. After a 3 minute incubation period, 1 μl of dNTP mix (0.125 mM each of each of the our dNTPs) is added and the incubation is continued for 5 additional minutes.

The samples are then moved to room temperature and 40 μl of ligase mix (50 mM Tris/HCl (pH 7.6), 10 mM $MgCl_2$, 1 mM ATP, 5% PEG, 1 mM DTT containing 0.005 units T4 ligase/μl) is added. The tubes are mixed well and allowed to incubate at room temperature for 1 hour.

After ligation, the samples are transformed into *E. coli* as described in the section entitled "Transformation of Bacterial Cells". Individual transformants are analysed by isolation of plasmid DNA (small-scale) followed by restriction digestion analysis and/or by sequencing (see below).

Gel Electrophoresis of DNA

For polyacrylamide gel electrophoresis of DNA, the Tris-Borate-EDTA (TBE) buffer described by Bethesda Research Laboratories, Gaithersburg, Md. 20877, which consists of 89 mM Tris-89 mM borate (pH 8.3), 2.5 mM $Na_2EDTA$ is used. The gels used consisted of 5% acrylamide and 0.2% bis-acrylamide dissolved in 100 ml 1×TBE. To this solution, 0.225 ml of an aqueous 25% ammonium persulfate solution is added.

After adding 55 μl of N,N,N',N'-Tetramethylethylenediamine (TEMED), the solution is pipetted into a gel mold. A 0.75 mm comb and 0.75 mm spacers are used and approximately 0.5-1.0 μg of DNA is loaded per well. Electrophoresis is carried out at 150-250 volts in 1×TBE. After electrophoresis, the gel is stained in an aqueous solution of ethidium bromide (0.5 μg/ml) and the DNA is visualized on an ultraviolet transilluminator. The gel is photographed using a Polaroid camera and Polaroid 57 film (Polaroid Tech. Photo, Cambridge, Mass. 02139).

DNA is recovered from polyacrylamide gels as follows: the desired band, visualized by ethidium bromide staining, is cut from the gel, placed in an Eppendorf tube and minced with a teflon pestle. An equal volume of 0.5M ammonium acetate, 1 mM EDTA solution is added and the tube is incubated at 37° C. overnight. The following day, the tube is centrifuged at 14,000×g in a microfuge for 5 minutes at room temperature, the supernatant is removed, ½ volume of fresh elution buffer is added to the minced polyacrylamide and the contents are mixed by vortexing.

The tube is again centrifuged, as above, for 5 minutes and the supernatant removed and pooled with the supernatant from the first centrifugation. The pooled supernatants are passed over a small glass wool column to remove any residual polyacrylamide gel pieces and the DNA in the sample is precipitated two times consecutively, each time by addition of 2 volumes of ethanol and incubation in dry ice-ethanol. The DNA is collected by centrifugation of the sample in a microfuge, as above, for 15 minutes at room temperature. The pellet is then resuspended in the buffer of choice depending on the nature of the next manipulation.

Agarose gel electrophoresis of DNA is performed in 1% agarose gels using the buffer described above for polyacrylamide gels. Ethidium bromide is added to the agarose to a final concentration of 0.5 μg/ml prior to pouring the gel. No ethidium bromide is included in the running buffer. After electrophoresis, the DNA is visualized on an ultraviolet transilluminator and photographed as described above. DNA is recovered from agarose gels by electroelusion onto DEAE-cellulose paper (Schleicher & Schuell, Inc. Keene, N.H. 03431, Cat# NA45). The DNA is eluted from the paper by incubation at 65° C. in 1×Tris-EDTA (TE) 10 mM Tris/HCl, 1 mM EDTA, pH 8.0) containing 150 mM NaCl for 15-20 minutes. To aid the elusion of the DNA, the contents of the tubes are mixed by vortexing them for 30 seconds every 5 minutes of incubation. The eluted DNA is precipitated by addition of 2 volumes of ethanol and incubation of the resultant mixture in a dry ice-ethanol bath until the contents in the sample becomes a slurry. The DNA is pelleted by centrifugation of the tubes in a microfuge at 14,000×g for 15 minutes at room temperature and resuspended in 150 μl TE. The resuspended DNA is extracted once with phenol:ChCl$_3$:isoamyl alcohol (25:24:1) and the aqueous phase is transferred to a fresh tube. The aqueous solution is made 0.3M with respect to sodium acetate by addition of 3.0M sodium acetate and the DNA is precipitated by addition of 2 volumes of ethanol as before. After centrifugation, as already described, the resulting DNA pellet is resuspended in the appropriate buffer depending on the next manipulation.

Transformation of Bacterial Cells

Transformation of E. coli with plasmid DNA is performed as described by Davis et al., A Manual for Genetic Engineering. Advanced Bacterial Genetics, Cold Spring Harbor Laboratory, Cold Springs Harbor, N.Y., (1982). Cultures are grown from single colonies of E. coli in a rich medium (i.e., Luria-Bertani (LB) medium) to early log phase (OD 550=about 0.3). The bacterial cells are pelleted by centrifugation in a clinical centrifuge at 1,400×g for 10 minutes at 4° C. The cells are resuspended in ½ volume of ice-cold CaCl$_2$ (50 mM) solution by gentle vortexing, and the resulting suspension is incubated on ice for 20 minutes. The cells are collected again by centrifugation as above and resuspended in 1/20 volume ice-cold CaCl$_2$. These are now competent E. coli cells.

Ligation mixtures are diluted at least 50% with TE prior to adding competent E. coli cells. Typically, a 1, 2, and 5 μl aliquot of each ligation mixture is placed in pre-chilled, sterile Eppendorf tubes and TE is added to a final volume of 10 μl. E. coli cells (200 μl of competent cells) are added to each tube and the tubes are incubated on ice for 40 minutes. The transformation tubes are heat shocked by incubation for 2 minutes at 42° C. after which they are returned to ice for 2-3 minutes. One ml of rich medium is added to each tube and the tubes are incubated at 37° C. for 30-60 minutes.

The cells are pelleted by gentle centrifugation (in a microfuge at 7,000×g), most of the medium is decanted and the pelleted cells are resuspended in the 100-200 μl of medium left in tube.

The contents of each transformation tube are spread on an LB-agar plate containing 100 μg/ml of ampicillin or the required amount of other antibiotics as appropriate (antibiotic plates). The antibiotic-resistant cells which grow are analyzed for the presence of the appropriate DNA construct by isolation of plasmid DNA (small scale), restriction enzyme analysis (below) and by sequence analysis (below).

Preparations of Plasmid DNA

1. Large Scale Isolation of Plasmid DNA

Plasmid-harboring strains of gram negative bacteria are grown to saturation overnight at 37° C. in LB medium (described by Maniatis et al., Molecular Cloning: a Laboratory Manual, p 440, Cold Spring Harbor Laboratory, Cold Spring Harbor, N.Y. (1982)), containing 125 μg/ml ampicillin or the appropriate concentration of whatever antibiotic is used. The bacterial cells are harvested by centrifugation, as above, washed once with 10 mM MgSO$_4$, collected again by centrifugation, then lysed by an alkaline lysis procedure essentially as described by Maniatis et al., supra. The procedure is as follows:

The cells from a 500 ml culture are resuspended in 10 ml of ice-cold lysis solution and incubated at room temperature for 5 minutes. Lysis solution consists of 50 mM glucose, 25 mM Tris/HCl (pH 8.0), 10 mM EDTA and 5 mg/ml of lysozyme, the lysozyme being added just prior to use. After the addition of 20 ml of a solution of freshly-made, ice-cold 0.2N NaOH, 1% sodium dodecyl sulfate (SDS) the contents are thoroughly mixed and incubated on ice for 10 minutes. Then, 15 ml of a 5M potassium acetate solution is added, and the contents are mixed by vortexing for 30 sec. The mixture is then incubated on ice for an additional 10 minutes. The 5M potassium acetate solution is prepared by addition of 60 ml of 5M potassium acetate and 11.5 ml of glacial acetic acid to 28.5 ml of H$_2$O. The resulting solution is 3M with respect to potassium and 5M with respect to acetate.

The tubes are then centrifuged at 47,500×g for 20 minutes at 4° C. and the supernatant is transferred to a fresh tube. Nucleic acid is precipitated from the supernatant by addition of 0.6 volumes of isopropanol followed by incubation for 15 minutes at room temperature. The nucleic acid is pelleted by centrifugation at 12,000×g at room temperature for 30 minutes. The supernatant is discarded and the remaining nucleic acid pellet is washed once with 70% ethanol. The pellet is resuspended in 5 ml TE, and further purified as described below.

The resulting plasmid DNA is purified by banding it two times successively in cesium chloride-ethidium bromide (0.97 g/ml and 0.43 g/ml respectively) equilibrium density gradients by centrifugation at 220,000×g at 20° C. for 14-18 hours. The bands containing plasmid DNA are removed from the tubes by inserting a 23 gauge needle (connected to a 5 ml syringe) through the side of the tube. Ethidium bromide is removed from the sample by extraction with H$_2$O-saturated n-butanol. The extraction is repeated until there is no longer a visible pink color in the aqueous phase. The extracted plasmid DNA is mixed with 2.0 volumes H$_2$O to dilute the CsCl. The sample is then mixed with 2.5 volumes of 95% ethanol and placed at −70° C. for 30 minutes. The DNA is pelleted by centrifugation at 12,000×g for 30 minutes at 4° C. The DNA pellet is washed once with 70 percent ethanol then resuspended in 0.36 ml of 1×TE and transferred to an Eppendorf tube (1.5 ml). Sodium acetate (3M) is added to a final concentration of 0.3M (1/10 volume) and the plasmid DNA is reprecipitated by the addition of 2 volumes of ethanol. The nucleic acid is pelleted by centrifugation and dissolved in a final volume of 0.5-2.0 ml of TE and stored at −20° C.

2. Small Scale Isolation of plasmid DNA

Each of a number of single, well-isolated antibiotic-resistant bacterial colonies from antibiotic plates is used to innoculate separate tubes containing 2 ml of LB medium with ampicillin at 125 μg/ml or other antibiotic and the resulting cultures are grown for at least 4 hours at 37° C. with shaking.

Bacteria from the same culture are streaked on an antibiotic plate and incubated at 37° C. overnight. This is called a master plate and will be the source of bacteria for subsequent manipulations. To obtain plasmids from them, the cultures are processed as follows: A portion of each culture (typically 1.5 ml) is transferred to a 1.5 ml Eppendorf tube and the cells are harvested by centrifugation at 14,000×g for 1 minute. The pelleted cells are resuspended in 100 µl of ice-cold, lysis solution (previously described) to which 4 mg/ml lysozyme is added just prior to use. The tubes are incubated at room temperature for 5 minutes, then 200 µl of a solution of freshly made, ice-cold 0.2N NaOH, 1% SDS are added. The tubes are mixed by inversion several times followed by incubation on ice for 5 minutes. Then, 150 µl of a 5M potassium acetate solution (previously described) is added, and the contents of the tubes are mixed by vortexing for 10 seconds while the tubes are in an inverted position.

After they are incubated on ice for an additional 5 minutes, the tubes are then centrifuged at 14,000×g for 5 minutes at 4° C. The supernatant is transferred to a fresh tube and extracted with an equal volume of phenol:CHCl$_3$:isoamyl alcohol (25:24:1). The tubes are again centrifuged, as above, at room temperature for 5 minutes in a microfuge and the aqueous phase is transferred to a fresh tube. The nucleic acid is precipitated from the solution by addition of 2 volumes of absolute ethanol, mixing by vortexing for 10 sec, and incubation for 2 minutes at room temperature. The tubes are again centrifuged, as above, at room temperature for 5 minutes. The ethanol is removed and the remaining nucleic acid pellet is washed once with 70% ethanol. The pellet is resuspended in 50 µl of TE containing 20 µg/ml RNase A.

The presence of the desired plasmid is determined by digestion of a 10 µl aliquot of the recovered DNA with the appropriate restriction endonucleases. The fragments produced in the digestion are analyzed by electrophoresis on agarose or polyacrylamide gels as described above. The master plate is used to initiate cultures originating from single colonies for large scale isolation of the plasmid and also for the preparation of bacterial stocks which are stored at −70° C. in LB medium containing 20% glycerol.

DNA Sequence Determination and Analysis

Plasmid DNA was prepared as described above for large scale isolation. The protocol used is a combination of the method of Zagursky, et al. (*Gene Anal. Tech.*, 2:89-94 (1985)) and the method supplied with the Sequenase® Sequencing Kit (Cat. #70700) available commercially from U.S. Biochemical Corp., Cleveland, Ohio 44122. The plasmid DNA is sequenced as follows: Three µg of an aqueous plasmid sample, in a total volume of 8 µl, is placed into a tube, 2 µl of 2N NaOH is added and mixed well. The tubes are incubated at room temperature for 5 minutes after which 1 µl of a primer oligonucleotide, 6 µl of H$_2$O, and 3 µl of 3M NaOAc (pH 5.2) are added and the samples are mixed. The plasmid and primer are co-precipitated by addition of 75 µl ethanol and incubation in a dry ice/ethanol bath for 20 minutes. The nucleic acids are pelleted at 14,000×g for 5 minutes at room temperature. The pellet is resuspended in 8 µl H$_2$O and 2 µl of 5×Sequenase® buffer is added. Sequenase® buffer (5×) is 200 mM Tris/HCl pH 7.5, 100 mM MgCl$_2$, 250 mM NaCl. These are called the annealing tubes.

The samples are incubated at 65° C. for 2 minutes and allowed to slowly cool to room temperature by placing the samples in a beaker of 65° C. H$_2$O and allowing the H$_2$O to cool at room temperature. While the samples are cooling, 4 tubes are labelled for each reaction (one each G, A, T, and C) and 2.5 µl of the 4 termination mixes (supplied with the kit) is added to the appropriately labelled tubes and the tubes are capped. These are called the termination tubes. Termination mixes all contain 160 µM dITP, 80 µM, dATP, 80 µM dCTP, 80 µM dTTP and 50 mM NaCl. In addition, the G termination mix contains 1.6 µM ddGTP, the A termination mix contains 8 µM ddATP, the T termination mix contains 8 µM ddTTP, and the C termination mix contains 8 µM ddCTP. The termination tubes are then prewarmed to 37° C.

After the annealing tubes cool to below 35° C., 1 µl of 100 mM DTT, 2 µl labeling mix, and 0.5 µl of $^{35}$S-dATP (500 Ci/mmol) are added and the tubes are mixed. Labeling mix is 3 µM dITP, 1.5 µM dCTP, and 1.5 µM dTTP. The Sequenase® enzyme is then added (6.5 units/annealing), the samples are mixed and incubated at 37° C. for 5 minutes. These are now called the labeling tubes. The contents of the labeling tubes are then aliquoted into the termination tubes 3.5 µl into each (G, A, T, C), and the incubation is continued at 37° C. for an additional 5 minutes. After the termination reaction, 4 µl of stop solution is added. Stop solution is 95% formamide, 20 mM EDTA, 0.05% bromphenol blue, and 0.05% xylene cyanol.

The samples are heated to 75° C. for 2 minutes and electrophoresed on a 6% polyacrylamide sequencing gel. The gel is 6% polyacrylamide (acrylamide:bisacrylamide=19:1), 8M urea, and 1×TBE buffer (see above). The running buffer is also 1×TBE. The gel is electrophoresed at 22 mA (constant current, dried down on Whatman 3MM chromatograpy paper and exposed to Kodak XAR X-ray film for 1-2 days at room temperature.

Plasmid Constructions

Plasmids may be constructed using restriction enzymes, polymerases and other procedures as described above and which are well known to those skilled in the art and described in Maniatis et al., supra. The promoter fragments of DNA of this invention may be obtained by digesting plasmid pEAS41.8 which has been deposited in the American Type Culture Collection, Rockville, Md. 20852-1776, accession number 67647, with the restriction endonucleases AhaII and SalI and isolating resulting DNA fragments with about 1500 and 354 bp. These fragments are joined together, in the proper orientation and order (hereafter referred to as the 1850 bp promoter fragment) and placed 5' to a reporter gene or any gene whose expression is to be controlled by abscisic acid. The construct resulting from the linkage of the promoter fragment of DNA and a desired gene may be placed in a plasmid vector capable of growing in bacteria, for convenience in preparing quantities of the construct. The 1850 bp promoter fragment of DNA may be further reduced in length to contain 640 bp, 254 bp or 50 bp by suitable enzymatic digestions, isolations and ligations. When operably linked to a gene or DNA sequence, said 640 bp, 254 bp and 50 bp promoter fragments retain their ability to respond to the presence of suitable concentrations of ABA. The molecular manipulations of DNA to construct the plasmids disclosed below were done as described in the section above and include digesting DNA with specific endonucleases, isolating fragments from gels, filling-in certain restriction site overhangs, ligating desired DNA fragments, and transforming bacterial cells. Several such plasmids are produced in the EXAMPLES but these are not meant to be all inclusive.

Isolation of Protoplasts

Rice suspension cultures, initiated from immature embryos or anther-derived callus, are maintained by weekly subculture at a 1:4 dilution ratio with fresh liquid N6 medium as described by Chu et al., *Sci Sinica* 18: 659–668 (1975) containing 2 mg/ml 2,4-dichlorphenoxyacetic acid and 3% (w/v) sucrose, pH 6.0. Protoplasts are isolated from suspensions of rice cells 4–6 days after subculture by overnight incubation (16–18 h) in 4 ml of enzyme solution per gram of cells and agitation of the mixture on a rotary shaker at 30 rpm at 25° C. The enzyme solution contained 2% (w/v) cellulase "Onozuka" RS and 0.5% (w/v) Macerozyme (both from Yakult Honsha, Nishinomiya, Japan) and 13% (w/v) mannitol, pH 5.6. Released protoplasts are filtered through a 60 μm mesh size nylon screen, transferred to 50 ml Pyrex test tubes and washed twice by centrifugation at 80×g for 10 minutes in Krens' F solution (140 mM NaCl, 3.6 mM KCl, 0.75 mM $Na_2HPO_4 \cdot 7H_2O$, 5 mM glucose, 125 mM $CaCl_2$, pH 7.0). Protoplasts are purified by resuspending the pellet in N6 medium with 17% (w/v) sucrose, centrifuging at 80×g for 20 minutes and collecting the floating layer. Cell counts are made with a Fuchs-Rosenthal hemocytometer.

Transformation of Protoplasts

Protoplasts are transformed as follows: Protoplasts ($1-5 \times 10^6$) are centrifuged gently (80×g) for 2 minutes in sterile tubes. The supernatant is removed and discarded and the tubes are shaken gently to loosen the protoplasts from the bottom of the tube. The DNA sample, with which the protoplasts are to be transformed, in 5 μl or less of TE, is added to the protoplasts. The tubes are shaken gently to disperse the cells in the DNA solution then 100 μl of a solution containing 40% PEG (Polysciences Inc., Warrington, Pa. 18976, CAT#1102) and 3 mM $CaCl_2$ is added. The resulting mixture is mixed gently for 10 seconds, then 1.0 ml of Krens' F solution is added to dilute out the PEG.

The tubes are incubated on ice for 15–20 minutes and then centrifuged at 80×g for 4 minutes. The supernatant is removed and the protoplasts are washed once with 1.0 ml of a solution of Krens' F solution. The protoplasts are resuspended in protoplast medium (0.2 mM $KH_2PO_4$, 1 mM $KNO_3$, 1 mM $MgSO_4$, 1 μM KI, 0.1 μM $CuSO_4$, 10 mM $CaCl_2$, 10% mannitol, pH 6.5) at a density of $1 \times 10^6$ protoplasts per ml and incubated at 25° C., in the dark, for the desired periods of time, with or without ABA, phaseic acid, Compound C or Compound D.

GUS Assay

Protoplasts are harvested by centrifugation at 80×g, and are resuspended in 0.5 ml 1×GUS lysis buffer (50 mM $NaPO_4$ (pH 7.0), 10 mM 2-mercaptoethanol, 10 mM EDTA, 0.1% Triton X-100, 0.1% N-lauroylsarcosine). The suspension containing the lysed protoplasts is transferred to Eppendorf tubes and centrifuged in a microfuge at 14,000×g for 10 minutes. It is possible to freeze the suspension of lysed cells in the extraction buffer if the assay is to be performed at a later date. Forty-five μl of the supernatant is transferred to a tube containing 755 μl $H_2O$ for analysis of protein content. Protein content is determined using the Bio-Rad Laboratories, Richmond, Calif. 94804, microassay. For the assay, 0.2 ml of the dye concentrate is added to the 800 μl sample and the absorbance is measured on a spectrophotometer at a wavelength of 595 nm. A standard curve must be calculated using a protein such as bovine serum albumin and the amount of protein in the experimental samples is read off the standard curve. The protein content, so determined, is multiplied by a factor of 2 to give the protein content in 90 μl of extract (which is the amount of extract in a single time point of the assay-see below). Of the remaining supernatant fluid, 405 μl is transferred to a fresh tube for analysis of GUS activity.

The substrate for the assay is 4-methyl-umbelliferyl-β-D-glucuronide (4-MUG) and was obtained from Sigma Chemical Co., St. Louis Mo. 63178, Cat# 9130) in 1×GUS buffer. It is at a concentration of 1 mM in the assay. One/tenth volume (45 μl) of a pre-warmed (37° C.) 10 mM 4-MUG stock is added to the pre-warmed 405 μl protoplast extract, and a 100 μl aliquot is immediately transferred to a well of a 24-well microtiter dish containing 0.9 ml 0.2M $Na_2CO_3$. Similar aliquots are removed at 0.5 hour, 1 hour, and 2 hours or at 1 hour, 2 hours and 4 hours, and the microtiter dishes are stored in the dark between time points. The dishes may be examined for the fluorescence of 4-methyl umbelliferone (4-MU), the product of enzyme digested 4-MUG, by means of an ultraviolet transilluminator. Individual samples, from each time point, may be examined on a flourimeter for quantitative analysis. In the case where quantitative analysis is desired, the excitation wavelength should be set at 365 nm and the emission wavelength should be set at 455 nm. Standards of 4-MU (Sigma Chemical Co., Cat# 1508), are also measured on the fluorimeter (typically at concentrations of 100 nM and 1 μM) and the specific activity is calculated as the picomoles of 4-MU produced per μg protein per hour of assay.

Transformation of Plants

There are two general forms in which foreign genes can be expressed in plant cells; as fixed integrates into the nuclear DNA (genome) of the host cell (stable expression), or not integrated but freely active in the cell (transient expression). To test for stable expression of genes requires weeks or months to regenerate transformed tissue and in many cases considerable space in growth chambers and greenhouses to grow the required amount of tissue/plants. If one is testing the effect of numerous recombinant DNA constructs (e.g., 50–100) for regulation of the foreign genes in separately transformed plants, the time and space required becomes considerable. If on the other hand, one has fast (hours), reliable transient expression systems to quickly test in cells, in a preliminary screen, which of the 50–100 constructs would be the most likely ones to show the natural regulation in stable transformants, significant time and money would be saved. Such a system would be even more important for most monocots (including the cereals), since these plants cannot be regenerated from single cells. With the exception of rice (rice plants have been regenerated from protoplasts by Kyozuka et al., *Mol. Gen. Genet.*, 206:408–413 (1987)), genes introduced into single cells from monocots cannot be monitored in stable, transgenic monocot plants for regulatory sequences. Using the methods of this invention, one can determine if inducible cereal promoters can be recognized in rice protoplasts using a transient assay, and if so, to quickly determine those sequences that are required for the induction. Furthermore, such a transient assay would allow the rapid screening of numerous analogs of a chemical inducer of gene expression such as ABA, to optimize structure/expression activity. Knowing that the induction works in rice cells, and that the key regulatory regions of the gene and specific moieties of the chemical inducer have been initially identified, one could introduce these sequences into a relatively few stable transformants of rice. Confirmation of the correlation between results obtained in transient expression systems with those from stable integration is provided by the Ebert et al. and Ellis et al. references discussed supra. These two studies, one using a constitutive bacterial promoter, the other an inducible promoter from a plant, both operably linked to an easily measured reporter gene, CAT, demonstrate that transient assays in monocot (maize) cells can predict sequences that are regulatory in stable transformants of the dicot tobacco.

The main approach used to identify operative recombinant DNA constructs of general utility is to place regulatory sequences derived from monocots in cells that are easy to transform, i.e., dicots such as tobacco, to determine if their sequences are recognized in transgenic plants. In fact, the Ebert et al. and Ellis et al. references demonstrate that when a viral enhancer element was operably linked to a maize inducible promoter (Adhl), and this construct stably introduced into tobacco plants, stable transformants were successfully induced by low oxygen levels.

Similarly, we have introduced the Em promoter from wheat (monocot), operably linked to the reporter gene GUS, into tobacco plants via the bacterial vector *Agrobacterium tumefaciens* to test for ABA induction of GUS in stable transformants (transgenic plants). Since Em gene expression was initially detected only in embryo tissue of wheat seeds in response to ABA, the regulatory sequences within the promoter may specify ABA-regulated expression only in embryo tissue. To determine if both these regulatory components of the Em promoter (i.e., tissue specificity and ABA inducibility) are represented in the same or different segments requires analyses of GUS expression throughout the life cycle of transgenic plants. Although the regulatory sequence responsible for ABA induction can be determined from transient expression in single-celled protoplasts, those sequences responsible for tissue specificity must be determined in multi-cellular, transgenic plants. Initially, we introduced ABA-regulatory regions of the Em promoter (as defined in the transient assay) operably linked to GUS into the tobacco plant genome via Agrobacterium. We then determined that the regulation throughout the life cycle of tobacco was identical to the normal regulation of the Em gene in wheat. We precociously induced GUS expression in very young seeds by exposure to exogenous ABA, and have shown the expression of GUS in mature seed. We demonstrated that the region of the promoter responding to ABA in protoplasts (defined in the transient system) includes that region regulating tissue specificity in transgenic plants. In addition, this demonstrates that these regulatory sequences from the monocot wheat are recognized and operable in the dicot tobacco.

Chemical Inducers

To bring plant gene expression under external chemical control in the field requires that the chemical not only be able to induce specific gene expression in transgenic plants, but that the chemical have unique traits that will allow it to be effective under field conditions, e.g., light stable, ability to be translocated within the plant, etc. Equally important will be a lack of toxicity or additional physiological effects on the plant. For example, ABA is a natural growth regulator found in all seed plants (c.f., Davies, P. (Ed.) *Plant Hormones and Their Roles In Plant Growth and Development.*, Martinus Nijhoff Publ. (1987)). It is light sensitive and will have pronounced physiological effects when applied to certain plant parts (c.f., Zeevaart and Creelman, *Ann. Rev. Plant Physiol.*, 39:439–473 (1988)). For example, when sprayed on leaves, ABA will cause stomates to close and thereby prevent gaseous exchange between the plant and the atmosphere. ABA has also been shown to inhibit seen germination, and to play a role in bud/seed dormancy, leaf senescence and in responses of plants to various physical stresses such as temperature and water. Numerous compounds have been described that mimic the effect of ABA on one or more of these processes (or any other ABA-mediated process) and are referred to as "ABA-like". If ABA-like compounds are to be used as chemical inducers of selected genes at all stages, their effects on these key physiological processes must be minimized or eliminated.

The transient assay and the experiments with transgenic plants outlined above will provide excellent tests which will allow us to optimize for field applicability traits as well as gene inducibility effectiveness of chemical inducers that are ABA-like. For example, Compound C [2-fluoro-5-1-hydroxy-2,6,6-trimethyl-4-oxo-cyclohex-2-en-1-yl/-3-methyl-2,4-pentadienoic acid] differs from ABA by addition of a fluorine molecule in the structure, possibly making it more light stable. Compound D [1,4-dihydroxy-$\beta$,2,6,6-tetramethyl-2-cyclohexane-1-penta-cis-2,trans-4-dienoic acid] differs in the introduction of a hydroxyl in place of an oxygen. Both of these compounds are structurally very similar to ABA and are functionally "ABA-like", i.e., they both inhibit seed germination. Jung and Grossman reported (*J. Plant. Physiol.* 121:361–367 (1985) and *J. Agron. Crop Sci.* 153:14–22 (1984) that various terpenoid derivatives are very "ABA-like" in their ability to produce certain physiological effects, e.g., stomatal closure, increase leaf senescence and increased chilling/freezing resistance (Flores et al., *J. Plant Physiol.* 132:362–369 (1988)). These terpenoid derivatives are described in two German patents by Bliesener et al. (1981 - DOS P 31 43 721) and Sauter et al. (1981 - DOS P 31 43 720). The effect of two such derivatives, Compound E [1,4-Dioxaspira[4,5]dec-6-en-8-ol,2,7,9,9-tetramethyl-8-[3 methyl-4-(4-methyl-1,3-dioxolan-2-yl)-3-buten-1-ynyl]-] and Compound F [1,4 Dioxaspiro[4,5]dec-6-en-8ol,8-(5,5-dimethoxy-3-methyl-3 -penten-1-ynyl)-2,7,9,9-tetramethyl-] are clearly ABA-like when assayed for their ability to close stomates and promote leaf senescence (Jung and Grossmann, *J. Plant Physiol.*, 121:361–367 (1985)) as well as increased chilling and freezing resistance (Flores et al., *J. Plant Physiol.*, 132:362–369 (1988)). We could predict that all such ABA-like compounds might serve as chemical inducers of our Em promoter/GUS construct. Using our specific and rapid transient assay in protoplasts, a series of ABA-like chemical inducers, that may have reduced or no effects on the physiological processes mentioned above (separately determined in bioassays for these processes) can be tested for their ability to induce gene expression. Screening of numerous compounds at different concentrations through our transient assay and these bioassays could result in an ideal chemical inducer in the field, i.e., one which induces gene expression at a concentration that is without other effects on the plant or plant processes.

In addition to screening various ABA-like compounds for the most effective inducer, one can also identify in the transient assay, the smallest and most responsive promoter sequence to these compounds. One could delete sections of the promoter until the smallest fragment is identified, facilitating subsequent manipulations of this ABA-regulatory sequence into other promoters/genes. In addition, one can make base substitutions in this small fragment to further delineate the specificity of control for each inducer. The combined use of this rapid preliminary screen in protoplasts, with testing of the inducers on transgenic plants under field conditions will result in the optimal structure/function combination of chemical inducer and controlling sequence for ideal control of gene expression in the field.

Stable Transformation of Tobacco

In order to introduce DNA constructions into plants, the constructions are mobilized from *E. Coli* strain HB101 into *Agrobacterium tumifaciens*, strain LBA4404. *E. coli* strain HB101, harboring the plasmid pRK2013, is used as a helper for the plasmid mobilization in a triparental mating. LBA4404 is grown overnight at 28° C. in 5 ml of minimal A-sucrose medium (37.5 mM $(NH_4)_2SO_4$, 165 mM $KH_2PO_4$, 300 mM $K_2HPO_4$, 8.5 mM sodium citrate, 1 mM $MgSO_4$, 0.2% sucrose, 50 μg/ml thiamine). The HB101 derivatives are grown at 37° C. in Luria-Bertani (LB) broth containing the appropriate antibiotic for 3 to 6 hours (to approximately $6-8 \times 10^8$ cells/ml). The cells from all cultures are pelleted by centrifugation and resuspended in 5 ml LB broth (to remove antibiotics from the medium).

The bacterial strains are mixed as follows: 100 μl of each of the HB101 derivatives and 200 μl of LBA4404 are placed in a 1.5 ml microcentrifuge tube, mixed well and pelleted gently. The bacterial pellet is resuspended in 50 μl LB broth and the mixture is pipetted onto a sterile nitrocellulose disk (Millipore HA type filters). Each nitrocellulose disk is transferred to a stack of 6-8 sterile Whatman #1 filter paper disks to remove the excess liquid from the culture and thereby concentrate the bacteria in the mixture. The nitrocellulose disks are then laced onto LB agar in a 150 mm petri dish and incubated for approximately 16 hours at 28° C.

Following the incubation, the disk is sterily transferred to a 15 ml tube containing 5 ml 10 mM $MgSO_4$. The tube is vortexed to release the bacteria into the liquid. The bacteria (100 μl and 50 μl aliquots) are plated on 2 minimal A-sucrose plates containing the appropriate antibiotic(s) and incubated at 28° C. for 3 days. After the incubation, resistant colonies are selected and the presence of the desired construct is confirmed by preparation of plasmid DNA (small-scale procedure from above) followed by restriction enzyme analysis.

Recombinant DNA constructs are stably integrated into the nuclear DNA of tobacco via *Agrobacterium tumifaciens* infection of tobacco leaf disks. Standard aseptic techniques for the manipulation of sterile media and axenic plant/bacterial cultures are followed, including the use of a laminar flow hood for all transfers. Potted tobacco plants for leaf disk infections are grown in a growth chamber maintained for a 12 hour, 24° C. day, 12 hours, 20° C. night cycle, with approximately 80% relative humidity, under mixed cool white fluorescent and incandescent lights. Tobacco leaf disk infections are carried out essentially by the method of Horsch et al., *Science*, 227:1229-1231 (1985).

Young leaves, not fully expanded and approximately 6-10 cm in length are harvested with a scalpel from approximately 4-6 week old tobacco plants. The leaves are surface sterilized for 20 minutes by submerging them in approximately 500 ml of a 10% Clorox, 0.1% SDS solution and then rinsing them 3 times with sterile deionized water. Leaf disks, 8 mm in diameter, are prepared from whole leaves using a sterile paper punch.

Leaf disks are inoculated by submerging them for several minutes in 20 ml of a 1:20 dilution of an overnight YEB broth culture of Agrobacteria carrying the plasmid of interest. After inoculation, the leaf disks are placed in petri dishes containing 0.1N1B agar medium (Murashige Minimal Organics Medium (Gibco, Grand Island, N.Y. 14072) with 0.1 mg/l thiamine, 0.5 mg/l pyridoxine, 0.5 mg/l nicotinic acid, 8 gm/l agar, 0.1 mg/l naphthalene acetic acid (NAA), and 1 mg/l benzylaminopurine (BAP), pH 5.8). The plates are sealed with parafilm and incubated under mixed fluorescent and "Gro and Sho" plant lights (General Electric) for 3 days in a culture room maintained at approximately 25° C.

To eliminate Agrobacteria from the leaf disks and to select for the growth of transformed tobacco cells, the leaf disks are transferred to fresh 0.1N1B medium containing 500 mg/L cefotaxime and 100 mg/L kanamycin. Cefotaxime is kept as a frozen 100 mg/ml stock and added aseptically (filter sterilized through a 0.45 μm filter) to the media after autoclaving. A fresh kanamycin stock (50 mg/ml) is made for each use and is filter sterilized into the autoclaved media.

Leaf disks are incubated under the growth conditions described above for 3 weeks and then transferred to fresh media of the same composition. Approximately 1-2 weeks later shoots which develop on kanamycin-selected explants are excised with a sterile scalpel and planted in MX$^-$ medium (0.1N1B agar medium from above without hormones), containing 200 mg/l cefotaxime and 100 mg/L kanamycin. Shoots which root in kanamycin are transferred to soil and grown in a growth chamber as described above. As plants develop flower buds, each inflorescence is bagged to ensure self pollination.

Seeds of transformed plants are harvested at various developmental stages to assay for the expression of GUS. After removing the capsule from the plant, half the capsule wall is cut and removed using a sterile scalpel. Immature seeds are harvested by scraping them off the placenta into Ependorf tubes. This procedure is repeated for the other half of the capsule. Mature seed is freely released after forming a hole in the capsule wall. Seeds are ground in Ependorf tubes using disposable pestles (Kontes, Vineland, N.J. 08360) and 1 ml GUS lysis buffer. The samples are vortexed and then centrifuged at 14K rpm for 15 minutes. The supernatant is used for GUS enzyme assay and protein determination (see above).

To analyze the effect of ABA on expression of GUS in immature see, young seeds are harvested as described above and placed on MX$^-$ medium with and without $10^{-4}$M ABA. Seeds are incubated in darkness at 25° C. for 20-48 hours, then transferred into Ependorf tubes using disposable cell scrapers (Costar, Cambridge, Mass. 02139). Each sample is split into two Ependorf tubes, then ground and assayed as described above.

The present invention is further defined in the following EXAMPLES, in which all parts and percentages are by weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions.

EXAMPLE 1

Construction of plasmids pBM107 and pBM108

Plasmid pDH51 was disclosed in Pietrzak, et al., *Nucl. Acids Res.*, 14:5857–5868 (1986) and served as the source of Cauliflower Mosaic Virus (CaMV) 35S promoter sequence, a polylinker sequence and the CaMV 35S 3' region. Plasmid pRAJ260 served as the source of the *E. coli* uidA gene, which encodes a β-glucuronidase enzyme (GUS). This plasmid is described by Jefferson et al., *Proc. Natl. Acad. Sci.* (USA) 83:8447–8451 (1986). The coding sequence for the GUS gene was cleaved from the vector sequences by digesting pRAJ260 with the restriction enzyme PstI as described above. This digestion results in the GUS gene being present on a 1.8 kb fragment. One such fragment was then isolated from a 1% agarose gel, (described above) and ligated into PstI-digested pDH51. Individual plasmids were analyzed until one was identified in which the PstI insert was present in the same 5' to 3' orientation as the 35S promoter. The resulting plasmid, pBM107, contains the *E. coli* gene for GUS located between the CaMV 35S promoter sequence and the CaMV 35S 3' sequence. Plasmid pBM107 was then digested with the restriction enzymes SmaI and SalI. The 5' overhang of the SalI site was filled-in by incubation of the cleaved plasmid for 15 minutes at 37° C. with the Klenow fragment of DNA polymerase I and 16 μM deoxynucleotide triphosphates (dNTPs). The resultant blunt-ended fragment was ligated as described above, transformed into *E. coli* and a clone was identified in which the plasmid no longer contained a BamHI site. Such a clone would have lost the smaller fragment. This resulted in the removal of the restriction endonuclease sites SmaI, BamHI, XbaI, and SalI from the polylinker region of pBM107. The resulting plasmid is pBM108. This plasmid contains the GUS gene and the CaMV 35S 3' region on a 2099 bp KpnI fragment. The construction of this plasmid is diagrammed in FIG. 1.

Construction of plasmid pBM109

Figure 2:
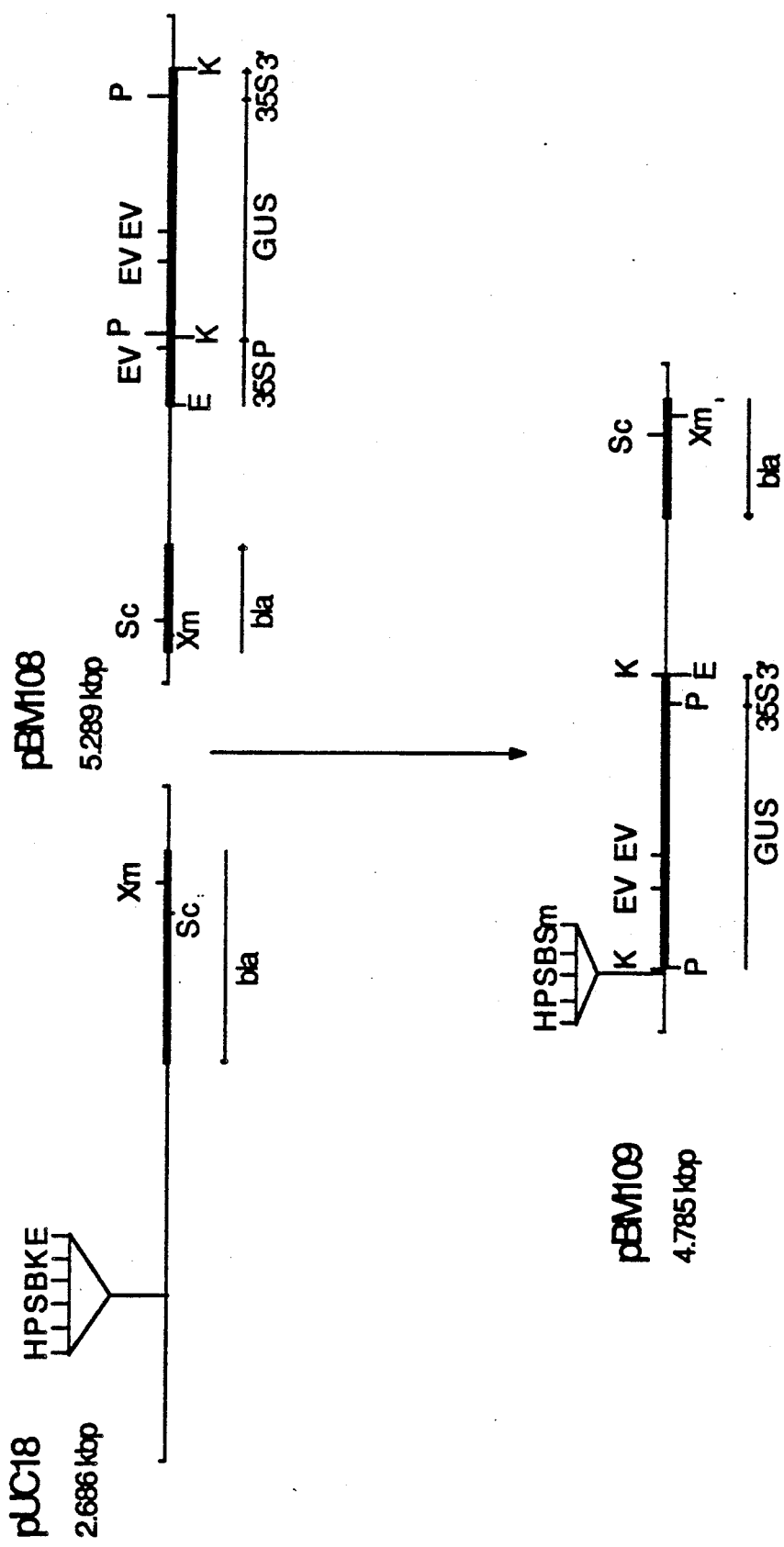
FIG. 2 is a physical map of plasmid pBM109 as derived from plasmids pBM108 and pUC18.

The 2099 bp KpnI fragment was cleaved from pBM108 with the restriction endonuclease KpnI, isolated on a 1% agarose gel as described above, and inserted into plasmid pUC18 at its KpnI restriction endonuclease site. The fragment was inserted in the opposite 5' to 3' orientation with respect to the lacZ gene which already resided in pUC18. The resulting plasmid, pBM109, is extremely useful because of the presence of multiple unique restriction sites just 5' relative to the GUS gene. Putative promoter sequences may be cloned into these sites thereby allowing the use of the GUS assay as a means of delineating promoter activity. Plasmid pBM109 has been deposited in the American Type Culture Collection (ATCC) Rockville, Md. 20852-1776 on Mar. 2, 1988 and bears the ATCC accession number 67648. The construction of this plasmid is diagrammed in FIG. 2.

Construction of plasmids pBM112 and pBM113

The source of the inducible promoter DNA sequence of the wheat Em gene is plasmid pEAS41.8, which has been deposited in the American Type Culture Collection (ATCC), Rockville, Md. 20852-1776 on Mar. 2, 1988 and bears the ATCC accession number 67647.

Plasmid pEAS41.8 was digested with the restriction endonuclease AhaII and the 5' overhang was filled-in as described. The plasmid was then digested with the restriction endonuclease SalI and electrophoresed on a 1% agarose gel. Two fragments were isolated: a SalI fragment of about 1500 bp and a SalI-AhaII fragment of 354 bp. This 354 bp fragment corresponds to positions 981-1334 of FIG. 3 and consists of 348 bp of Em promoter sequence plus 6 bp of Em coding region. The 1500 bp SalI fragment represented sequences from position 981 in FIG. 3 to a site about 1500 bp 5' of 981. The plasmid pBM112 was constructed by ligating the 354 bp SalI/blunt-ended AhaII fragment into SalI/SmaI digested pBM109.

Figure 4:
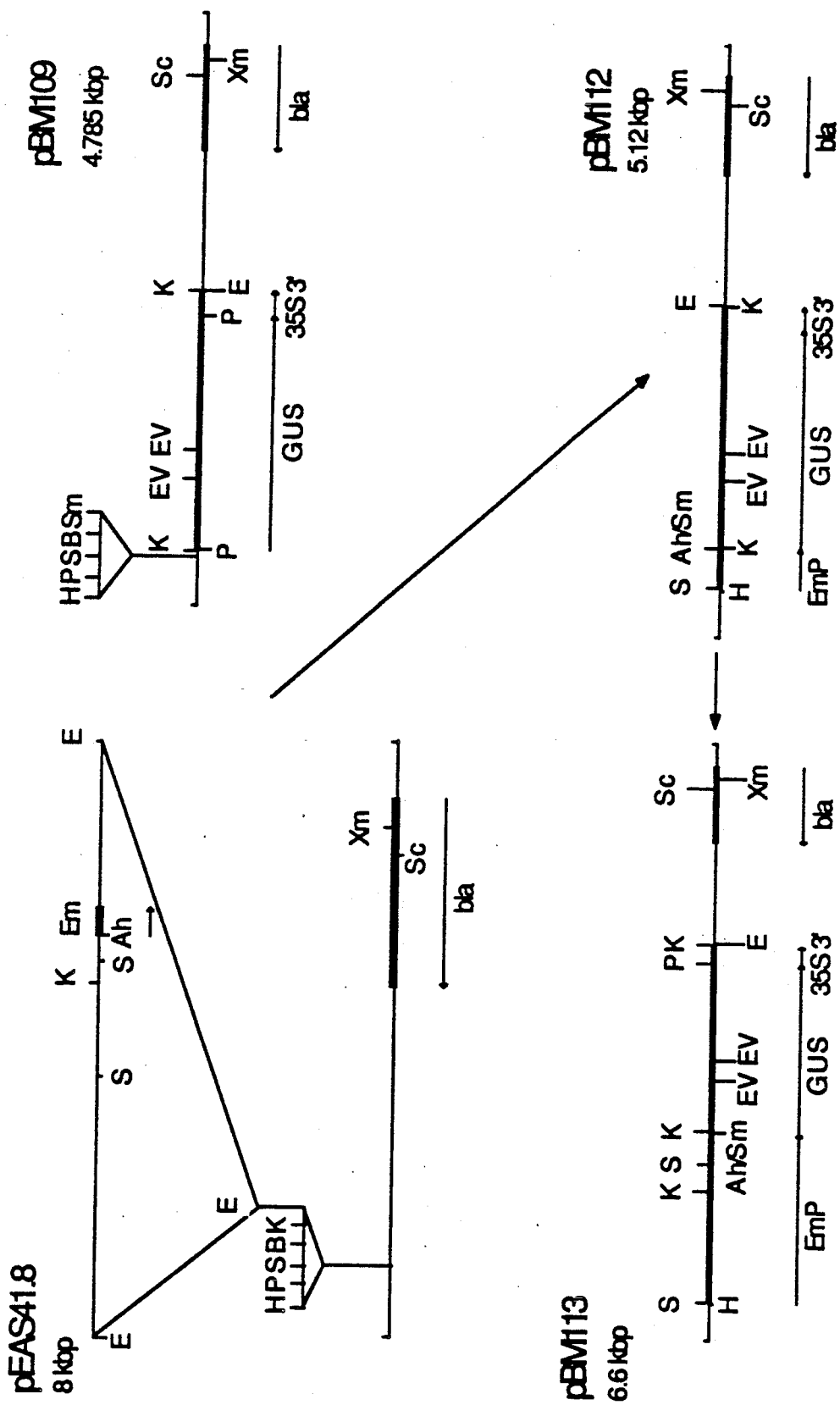
FIG. 4 is a physical map of plasmid pBM113 as derived from plasmids pBM109 and pEAS41.8.

The 1500 bp SalI fragment was then ligated into SalI-digested pBM112. A clone was identified in which the 1500 bp SalI fragment was in the proper orientation to the SalI/AhaII fragment and this plasmid is called pBM113. The construction of this plasmid, which contains the approximately 1850 bp promoter fragment, is diagrammed in FIG. 4. This SalI-SalI-AhaII fragment insertion resulted in the translational initiation codon (ATG) of the Em gene coding region being 5' relative to and in frame with the translational initiation codon for the GUS gene. Therefore, this fusion created a gene whose protein product is a chimera containing 12 amino acids added to the natural amino terminus of GUS (assuming the plant translation initiation signals are preferentially recognized in plant systems).

EXAMPLE 2

Construction of plasmids pBM113Kp and pBM311

Plasmid pBM109 was digested with 0.5 units KpnI/μg DNA (total reaction volume 50 μl) and 10 μl aliquots of the reaction were removed at time points of 2, 5, 10, 20 and 30 minutes of digestion. The aliquots were placed in tubes pre-warmed to 70° C. which contained 1 μl of 25 mM EDTA in agarose gel tracking dye. The aliquots remained at 70° C. for 10 minutes to stop the reaction. The aliquots, which contained partial digestion products, were then electrophoresed on a 1% agarose gel. The band which corresponded to linearized pBM109 (4785 bp) was eluted as already described.

Plasmid pBM113 was digested with the restriction endonuclease KpnI. This generated a 652 bp fragment of DNA containing a portion of the approximately 1850 bp of DNA from the wheat genome present. This 652 bp fragment represents 640 bp of Em promoter sequence, 6 bp of Em coding region and 6 bp of polylinker sequence. This 640 bp promoter fragment corresponds to position 689 to 1328 in FIG. 3. The 652 bp fragment was isolated and ligated into the linearized pBM109. This ligation should, theoretically, contain four different constructs due to the presence of two KpnI sites in pBM109 and the possibility that the 652 bp fragment, having two identical ends, could have inserted in either orientation in either site. Two of these constructs were to be isolated, namely, those into which the KpnI fragment had been inserted 5' relative to the GUS gene coding region, one in each orientation. After transforming E. coli with the ligation mixture, the transformants were screened for the appropriate constructs by small scale plasmid isolation, etc. as described above. The plasmid pBM113Kp contains the KpnI fragment in the forward orientation (with respect to the GUS gene) and has exactly reconstructed the junction found in the originating plasmid pBM113. Thus, plasmid pBM113Kp is a derivative of the plasmid pBM109 into which the 652 bp KpnI fragment of pBM113 has been inserted into the KpnI site 5' relative to the initiation codon of the GUS gene. The plasmid pBM311 contains the same 652 bp fragment in the same KpnI site but in the opposite orientation. The construction of these plasmids is diagrammed in FIG. 5.

EXAMPLE 3

Construction of Plasmids pBM113Δ220.10, pBM113Δ220.9, pBM113Δ240.13, and pBM117

Plasmid pBM113 was subjected to exoIII-mediated digestion as described in the section entitled "Endonuclease III-Mediated Deletion". Plasmid DNA (10 μg) was cleaved with HindIII to completion and the overhang was filled-in with a α-phosphorothioate nucleotides as described. The reaction was then extracted and the DNA ethanol precipitated, as described. The linearized, filled-in DNA molecule was then cleaved with BglII, which cleaves 683 bp 5' relative to the KpnI site. The sample was extracted and precipitated as described above. This produced a molecule which was resistant to exoIII digestion at the HindIII site but sensitive to exoIII digestion at the BglII site.

ExoIII digestion was performed on the prepared plasmid as described in the section entitled "Endonuclease III-Mediated Deletion" and aliquots were removed at 10 second intervals beginning at 40 second and continuing to 250 seconds. E. coli cells were transformed with the ligated samples from each time interval, and the transformed cells were plated on LB plates containing 100 μg/ml ampicillin. The plates were incubated at 37° C. overnight and placed at 4° C. the following day.

Bacteria originating from individual transformants from the samples of the various time intervals were analyzed by isolation of plasmid DNA (small scale) and restriction enzyme digestion. The isolated plasmids were digested with the restriction enzymes KpnI and PvuII concomitantly. These enzymes were chosen for the following reasons:

1. Deletions were not of interest until the KpnI site which defines the 5' border of the Em promoter fragment known to be present in pBM113Kp was lost. The loss of the KpnI site is indicative of the removal of sufficient DNA so that the fragment remaining has less of the promoter region than that in pBM113Kp.

2. The presence of two PvuII sites between the KpnI site mentioned above and the translational initiation codon (ATG) of the construct would allow estimation of the deletion endpoint using the sizes of the fragments produced upon digestion.

Figure 6:
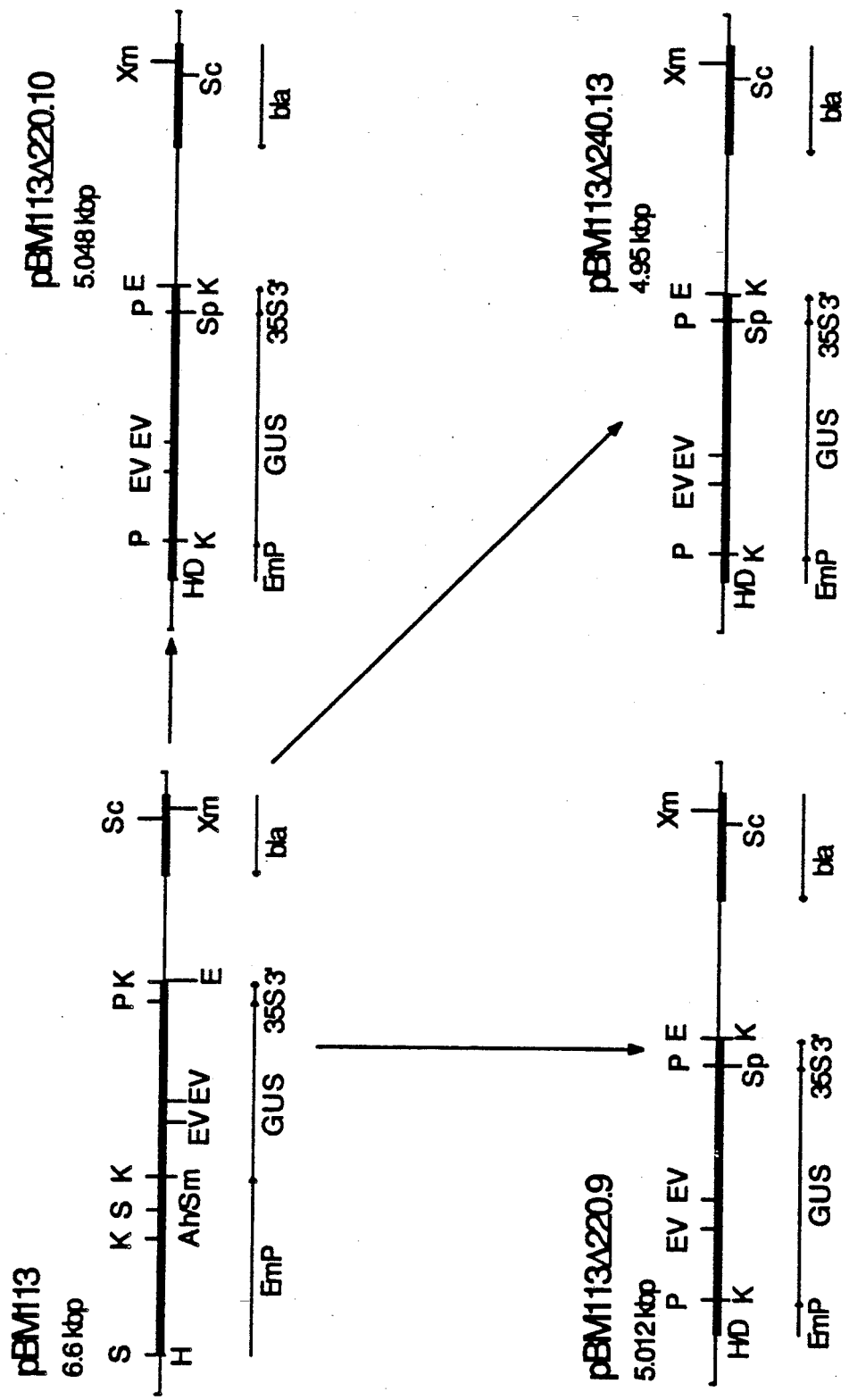
FIG. 6 is a physical map of plasmids pBM113$\Delta$220.10, pBM113$\Delta$220.9 and pBM113$\Delta$240.13 as derived from plasmid pBM113.

Several transformants harboring plasmids of interest were selected. The plasmids are named pBM113Δ220.10, pBM113Δ220.9, and pBM113Δ240.13. The construction of these plasmids is diagrammed in FIG. 6. [The Δ in the plasmid name refers to Deletion, and the number refers to the time interval (seconds) of digestion]. The endpoints of the deletions were determined by sequence analysis (see above) and found to be at −291 bp, −254 bp, and −192 bp from the translational initiation codon (ATG) of the Em gene, respectively. These positions correspond to positions 1038, 1075 and 1137 in FIG. 3, respectively.

Construction of Plasmid pBM117

Plasmid pBM117 is a derivative of the plasmid pBM109 into which the promoter region of the 35S gene of CaMV has been cloned. This was done by cleavage of plasmid pDH51 with the restriction endonucleases NcoI and SmaI.

The overhang produced by NcoI cleavage was filled-in as described in the section entitled "Enzymatic Treatments of DNA". The resulting fragments of the cleavage reaction were separated by electrophoresis on a 1% agarose gel and a fragment 535 bp in length, containing the 35S promoter region, was isolated from the gel as described in the section entitled "Gel Electrophoresis of DNA".

Figure 7:
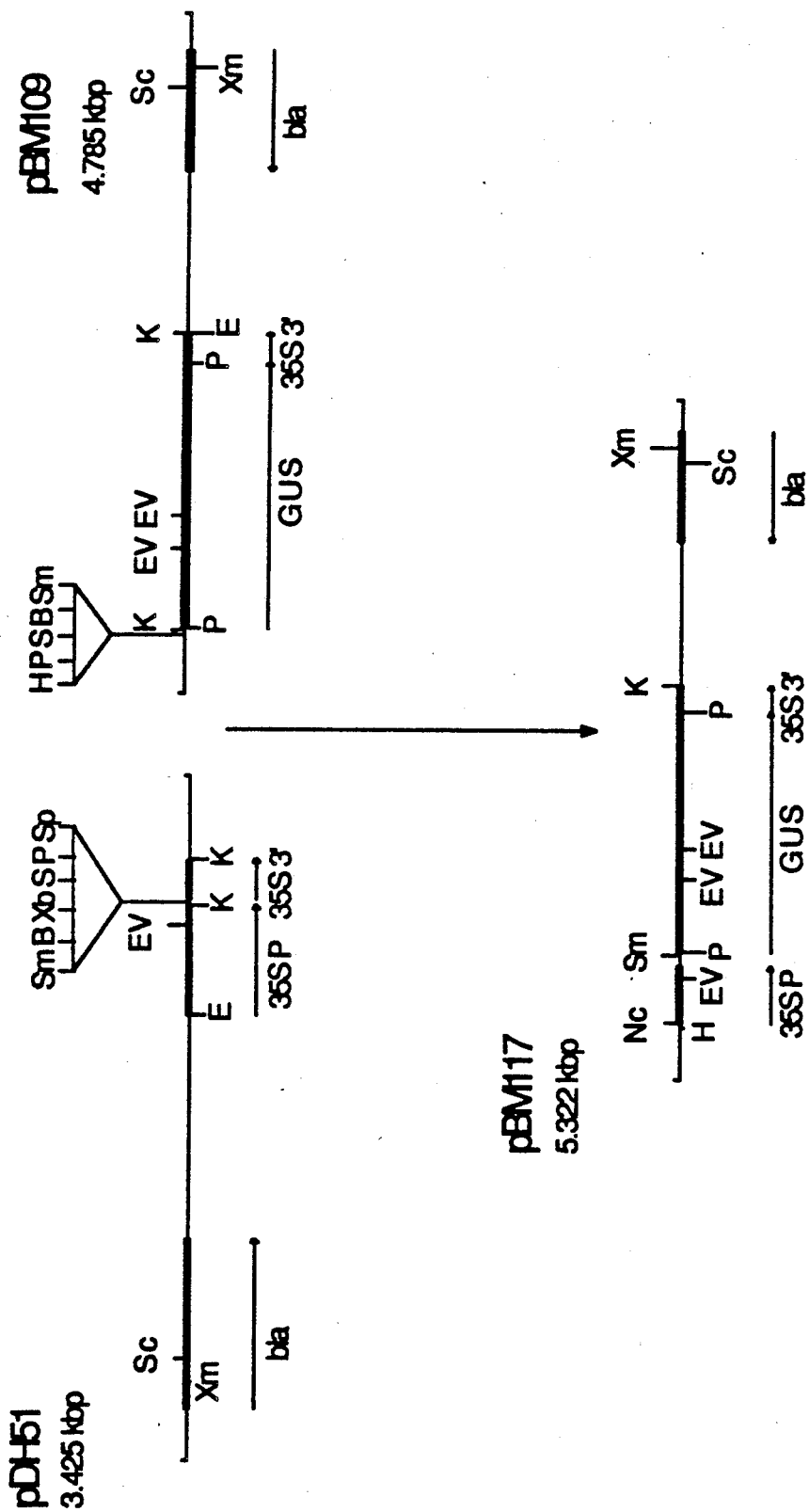
FIG. 7 is a physical plasmid map of plasmid pBM117 as derived from plasmids pDH51 and pBM109.

The plasmid pBM109 was cleaved with the restriction endonuclease SmaI which results in the linearization of the molecule. The 535 bp fragment isolated as described in the previous paragraph, was ligated (as described in the section entitled "Enzymatic Treatments of DNA") into the SmaI-cleaved pBM109. After transforming E. coli with the ligation mixture, as described in the section entitled "Transformation of Bacterial Cells", a cone was identified which harbored a plasmid containing the 35S promoter fragment of DNA, 5' relative to the GUS encoding region of DNA, and in the proper orientation. The construction of this plasmid is diagrammed in FIG. 7.

EXAMPLE 4

Construction of Plasmids pBM119, pCS102 and pBM120

Figure 8:
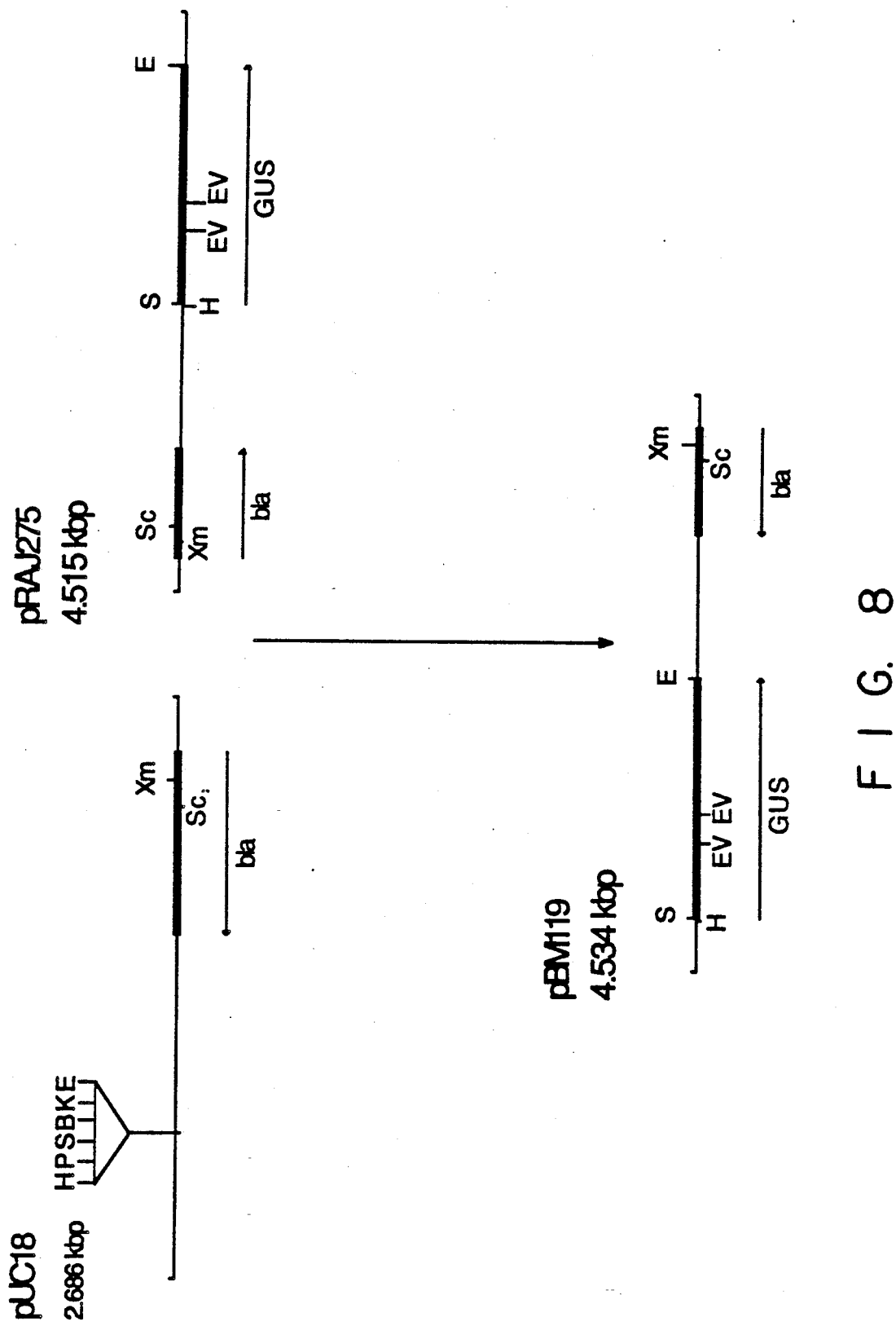
FIG. 8 is a physical map of plasmid pBM119 as derived from plasmids pUC18 and pRAJ275.

Plasmid pRAJ275 served as the source of the β-glucuronidase gene (GUS) and has been described by Jefferson in *Plant Molecular Biology Reporter* 5:387–405 (1987). The GUS gene in plasmid pRAJ275 differs from that in pRAJ260 in that the sequence surrounding the initiator codon ATG has been changed to introduce two new restriction sites, SalI, and NcoI and in the introduction of a single restriction site for the restriction enzyme EcoRI at the 3' end of the gene. The NcoI site contains the translational start codon (ATG) and is flanked immediately 5' by the SalI site. The GUS gene was cleaved from plasmid pRAJ275 by sequential cleavage of the plasmid, as described above, with SalI, after which the SalI site was filled-in as described above, followed by cleavage with EcoRI. This digestion results in the GUS gene being on a 1857 bp fragment. One such fragment was isolated from a 1% agarose gel (described above) and ligated into pUC18 which had been cleaved identically as was pRAJ275 (i.e., SalI digestion, after which the end was filled-in, followed by EcoRI digestion). Individual plasmids were analyzed until one was identified which carried the GUS gene and the resulting plasmid is pBM119. The construction of this plasmid is diagrammed in FIG. 8.

Plasmid pDH51, which served as the source of the 35S 3' sequences, was cleaved with the restriction enzymes NcoI and SphI after which the ends of the fragment were treated with T4 polymerase, as described, to create blunt ends. This treatment results in the liberation of a 568 bp fragment containing the 35S promoter region plus the polylinker region of pDH51 and a 2857 bp fragment consisting of the remainder of pDH51, which carries the 35S 3' end. The 2857 bp fragment was isolated from a 1% agarose gel, ligated, and individual plasmids were screened for the presence of a 214 bp EcoRI fragment which would carry the 35S 3' region. The resulting plasmid is pCS102. The construction of this plasmid is diagrammed in FIG. 9.

Plasmid pCS102 was cleaved with EcoRI and the 214 bp fragment carrying the 35S 3' end was isolated on a 1% agarose gel and ligated into EcoRI-cut pBM119. Individual plasmids were analyzed until one was isolated which carried the 35S 3'region 3' of the GUS gene and in the proper 5' to 3' orientation. The resulting plasmid is pBM120 and the construction of this plasmid is diagrammed in FIG. 9.

EXAMPLE 5

Construction of Plasmids pBM165 and pBM167

The series of plasmids designated pBM165 are derivatives of plasmid pDH51 into which an oligonucleotide (oligo) has been inserted into the 35S promoter region. The oligonucleotide was inserted into the EcoRV site at −90 bp from the start of transcription from the 35S promoter. The oligonucleotide was synthesized using an ABS DNA Synthesizer and includes a 25 bp region of the Em promoter bearing sequence homology to a region of a conglycinin promoter plus 19 bp of contiguous Em 5' flanking sequences and 7 bp of contiguous Em 3' flanking sequences. This 50 bp promoter sequence corresponds to coordinates 1091 to 1140 in FIG. 3. In addition, the ends of the oligo contain ½ an EcoRV site such that the oligo may be inserted into the EcoRV site and excised with the same enzyme. Therefore, the oligo is 56 bp in length, and is hereafter referred to as "the 56 bp oligo". To construct the pBM165 series of plasmids, the plasmid pDH51 was digested with the restriction enzyme EcoRV and ligated in the presence of the 56 bp oligo. Individual plasmids were analyzed for the presence of the oligo and plasmids were isolated in which the orientation and copy number of the oligo are as follows:

pBM165-2: This plasmid contains a single copy of the oligo in the same 5' to 3' orientation as the sequence occurs in the Em promoter.

pBM165-4: This plasmid contains two copies of the oligo, both of which are in the same 5' to 3' orientation as the sequence occurs in the Em promoter (i.e., head-to-tail).

Plasmids pBM165-2 has been deposited in the American Type Culture Collection (ATCC), Rockville, Md. 10852-1776 on Sept. 15, 1988 and bears the ATCC accession number 67797.

The series of plasmids designated pBM167 are derivatives of pBM120 into which the 35S promoter regions from the plasmids pBM165-2 and pBM165-4 have been inserted. Plasmids pBM120 was cleaved with the restriction enzyme SalI and the ends of the plasmid were filled-in as described. The plasmids pBM165-2 and pBM165-4 were cleaved with the restriction enzymes SmaI and EcoRI after which the EcoRI ends of the plasmid were filled-in as described. This digestion results in the 35S promoter fragment containing the 56 bp oligo being on a 599 bp fragment for plasmids pBM165-2and on a 655 bp fragment for plasmid pBM165-4. These fragments were isolated from a 1% agarose gel and were ligated to the SalI-cut, filled-in pBM120. Individual plasmids were analyzed and isolates were identified which had incorporated the promoter regions in the proper orientation. The number and orientation of oligonucleotide insertions were confirmed by DNA sequence analysis, as described above. These plasmids are the pBM167 series and they are as follows:

pBM167-11: This plasmid contains the promoter region from the plasmid pBM165-2.

pBM167-4: This plasmid contains the promoter region from the plasmid pBM165-4.

Figure 11:
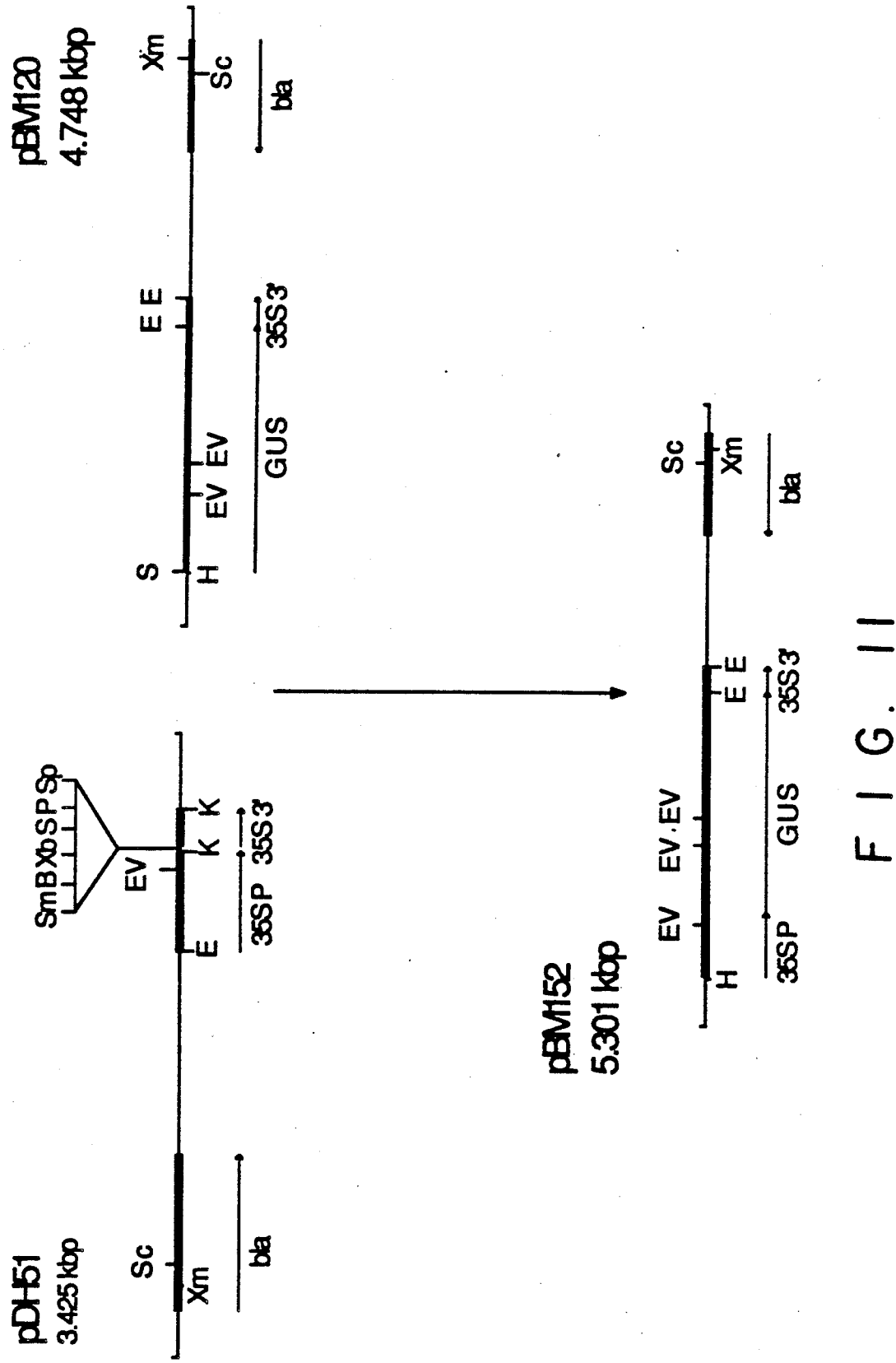
FIG. 11 is a physical map of plasmid pBM152 as derived from plasmids pDH51 and pBM120.

The construction of plasmid series pBM165 and plasmid series pBM167 are diagrammed in FIG. 10. The 35S promoter, not containing the 56 bp oligo, was isolated from pDH51 and inserted into plasmid pBM120 exactly as described for the construction of the plasmid series pBM167 above. The resulting plasmid is pBM152 and the construction of this plasmid is diagrammed in FIG. 11.

EXAMPLE 6

Construction of Binary Plasmids pBM1170, pBM1130 and pBM3110

Binary plasmids are plasmids which may be propagated in several hosts. Many plasmids of this type are useful for the Agrobacterium-mediated transformation of certain species of plants, especially tobacco. Binary constructs were made for the stable transformation of tobacco with several of the promoter-GUS constructs used in the transient system described above. The binary vector used for the construction of these binary plasmids was pBI101.1 and has been described by Jefferson et al. *EMBO* 6:3901-3907 (1987). Plasmid pBI101.1 is a derivative of plasmid pBIN19 into which a "promoter-less" GUS cassette has been inserted. Therefore, this plasmid has a plant selectable marker, in the form of a neomycin phosphotransferase gene (nptII), driven by the nopaline synthase promoter, which encodes resistance to the antibiotic kanamycin. All constructs were made by the ligation of gel-purified HindIII/EcoRI fragments.

Digestion of pBI101.1 with these two enzymes results in the liberation of an approximately 2 kbp fragment containing the "promoter-less" GUS cassette from the vector. This fragment is not used in the constructs. The remaining vector fragment (approximately 10 kbp) was gel purified as described above. Digestion of plasmid pBM117 with the same two enzymes results in the liberation of a 2687 bp fragment from the vector sequences containing a 35S promoter-GUS-35S 3' cassette. This 2687 bp fragment will be called fragment A. Similarly, digestion of the plasmids pBM113Kp and pBM311 with the same enzymes results in the liberation of 2801 bp fragments from the vector sequences. These fragments (B And C, respectively) contain the Em promoter-GUS-35S 3' cassettes with the Em promoter in the forward orientation in fragment B and in the reverse orientation in fragment C. All three of these fragments (A, B and C) were individually ligated into the binary vector sequences purified above (the approximately 10 kbp fragment from pbI101.1).

Figure 12:
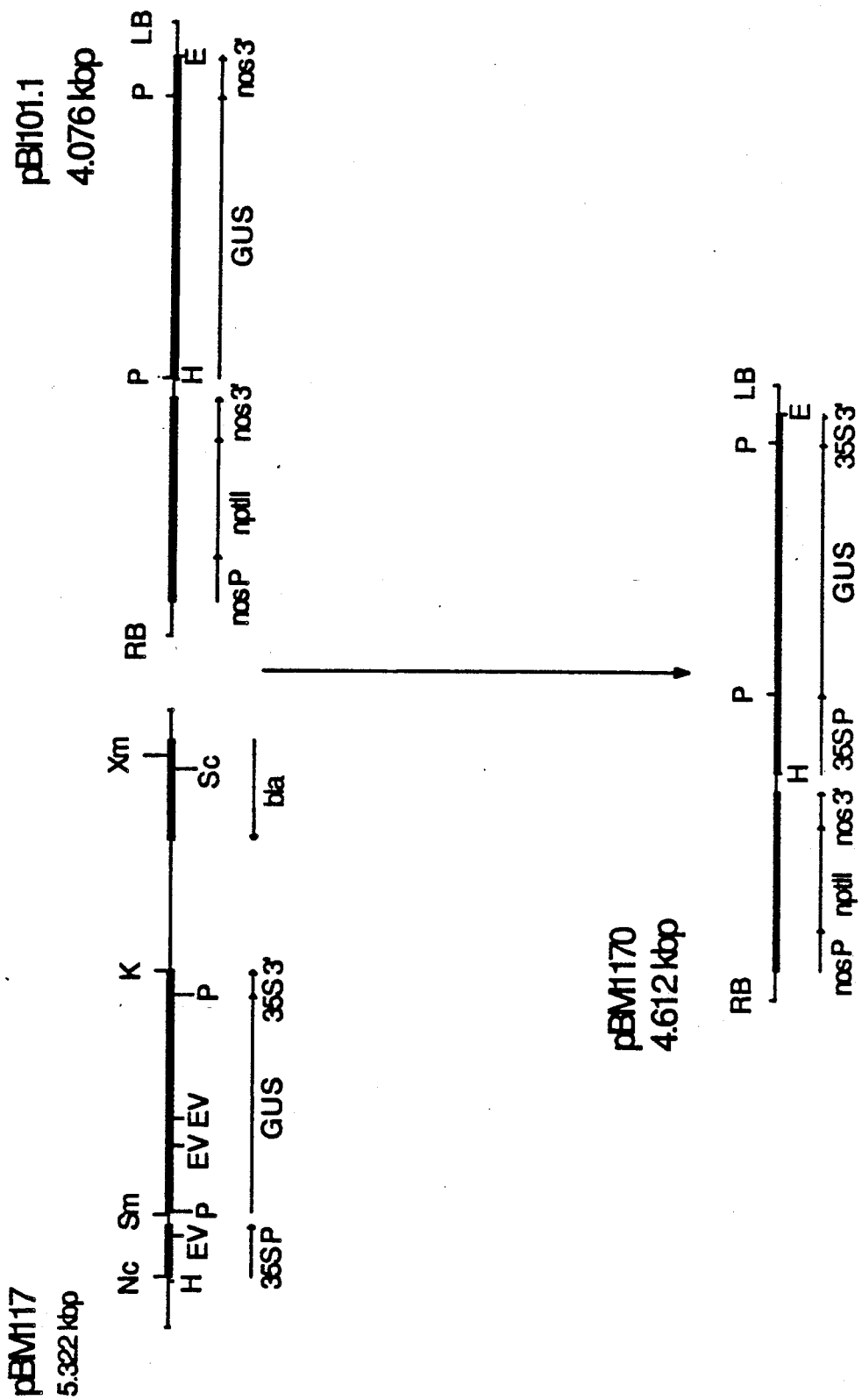
FIG. 12 is a physical map of plasmids pBM1170 as derived from pBM117 and pBI101.1.
Figure 14:
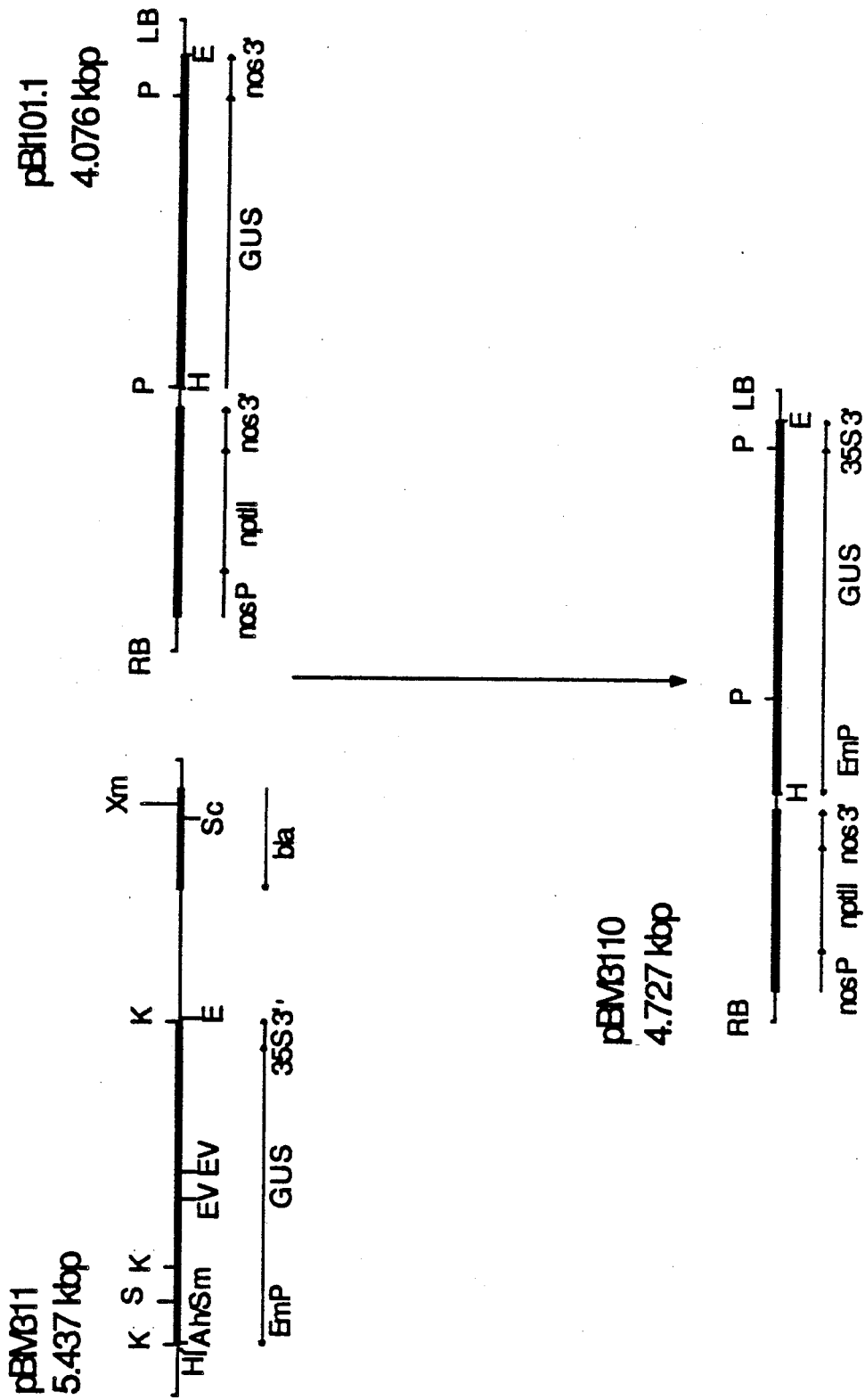
FIG. 14 is a physical map of plasmid pBM3110 as derived from plasmids pBM311 and pBI101.1.

Individual binary plasmids were identified which now contained the relevant promoter-GUS cassette. As such, these plasmids now contain a selectable plant marker (kanamycin resistance) and an appropriate cassette containing an experimental promoter-GUS-35S 3' construct. Plasmids pBM1170, pBM1130 and pBM3110 are binary derivatives of plasmids pBM117, pBM113Kp and pBM311, respectively. The construction of these plasmids are diagrammed in FIGS. 12, 13 and 14, respectively. These binary constructs were introduced into the Gram-negative bacterium *Agrobacterium*

*tumifaciens* by the method of tri-parental mating and subsequently introduced into tobacco tissue by the method of leaf disk transformation (see section on "Transformation of Plants" and "Stable Transformation of Tobacco").

EXAMPLE 7

Response of an 1850 bp Promoter Fragment (pBM113) to ABA

Protoplasts were isolated, as described in the section entitled "Isolation of Protoplasts" from a suspension culture of rice. The protoplasts were either not exposed to DNA or were transformed with plasmid pBM113 DNA as described above in the section entitled "Transformation of Protoplasts". The culture of protoplasts which did not receive DNA contained $1 \times 10^6$ protoplasts. The culture to be transformed with plasmid DNA contained $4 \times 10^6$ protoplasts and these were exposed to 4 μg of pBM113 plasmid DNA. The culture with $1 \times 10^6$ protoplasts, which served as a control, was resuspended in a 1.0 ml of protoplasts medium after the transformation protocol and was incubated for 2 days. The culture containing transformed protoplasts was split into 4 equal aliquots each containing $1 \times 10^6$ protoplasts and the 4 aliquots were incubated in protoplast medium either lacking ABA, or containing $10^{-5}$M ABA, $10^{-6}$M ABA, or $10^{-7}$M ABA, respectively. These cultures were also incubated for 2 days.

After the 2 days incubation, the protoplasts were collected by centrifugation at $80 \times g$. The protoplast medium was removed from the tubes and the cells were lysed by addition of 0.5 ml of GUS lysis buffer as described in the section entitled "GUS Assay". Each culture of lysed protoplasts was then assayed for GUS activity as described above in the section entitled "GUS Assay". The specific plasmid DNA with which the protoplast were transformed, the presence or absence of ABA, the concentrations of ABA in which the cultures were incubated and the results from the assay are given below in Table 1.

TABLE 1

| | Treatment | | |
|---|---|---|---|
| Sample | Source of Input DNA | [ABA] | Specific Activity* (Units) |
| (1) | NO DNA | 0 | 0.25 |
| (2) | pBM113 | 0 | 3.87 |
| (3) | pBM113 | $10^{-5}$M | 1167.65 |
| (4) | pBM113 | $10^{-6}$M | 251.42 |
| (5) | pBM113 | $10^{-7}$M | 4.74 |

*Ten units are equivalent to 5.57 pmoles of 4-MU/μg protein/hour in this experiment.

The results shown in Table 1 demonstrate the following points:

1. There is no significant endogenous GUS activity in the protoplasts in the absence of DNA (Treatment Sample 1).
2. There is a 300-fold increase in the level of expression generated by the fragment of the Em promoter in the presence of the highest concentration of ABA relative to the level of expression in the absence of ABA (Compare Treatment Samples 2 and 3).
3. The level of induction of the Em promoter-GUS construct is dependent on the concentration of ABA in the medium (Treatment Samples 3-5).

Therefore, there is an induction of GUS expression in protoplasts containing the Em promoter-GUS construct (plasmid pBM113) only when ABA is present in the medium. In addition, the level of induction is dependent on the concentration of ABA.

EXAMPLE 8

Time course of ABA Effect

The source of protoplasts used for transformation is identical to that used in EXAMPLE 7. Protoplasts either did not receive added DNA or they were transformed with plasmid DNA as described in the section entitled "Transformation of Protoplasts".

For those protoplasts which did not receive exogenous DNA (i.e., no DNA in Table 2) a culture containing $2 \times 10^6$ protoplasts were subjected to the transformation protocol except that it did not receive any DNA. The culture was then divided into 4 equal aliquots (each containing $0.5 \times 10^6$ protoplasts). Two of these four aliquots were incubated in protoplast medium without ABA while the other two contained $10^{-5}$M ABA. The protoplasts from two samples, one without ABA and one with ABA, were collected immediately after protoplast medium was added. The protoplasts in the other two samples, one without ABA and one with ABA, were collected after 6 hours of incubation in the dark at 25° C.

For those protoplasts which received pBM117 plasmid DNA (to serve as the positive control), a culture containing $2 \times 10^6$ protoplasts was transformed with 2 μg of plasmid DNA then divided and incubated as the cultures above which did not receive DNA (i.e., the four samples were harvested either immediately after addition of protoplast medium (one each, without ABA and with ABA) or at 6 hours (again, one each, without ABA and with ABA)).

The plasmid pBM113 contains the 1850 bp promoter sequence of this invention operably linked to the GUS gene. A protoplast suspension containing $5 \times 10^6$ protoplasts was transformed by the addition of 5 μg of plasmid DNA during the transformation protocol.

The protoplast suspension was split into 2 equal aliquots ($2.5 \times 10^6$ protoplasts each), one without ABA and one with ABA ($10^{-5}$M) and incubated as described.

Samples from the protoplast cultures ($0.5 \times 10^6$ protoplasts), one each, without ABA and with ABA, were removed immediately after the addition of protoplast medium, and at 1, 2, 4, and 6 hours of incubation. All the protoplast samples were stored at $-70°$ C. after collection in GUS lysis buffer and assayed the following day for the presence of GUS activity as described in the section entitled "GUS Assay". The results are shown in Table 2.

TABLE 2

| Treatment | | Specific Activity* (Units) | | | | |
|---|---|---|---|---|---|---|
| Source of Input DNA | [ABA] | 0** | 1** | 2** | 4** | 6** |
| NO DNA | 0 | 0.30 | ND*** | ND | ND | 0.11 |
| pBM117 | 0 | 0.30 | ND | ND | ND | 10.00 |
| pBM113 | 0 | 0.17 | 0.55 | 1.91 | 5.99 | 36.31 |
| NO DNA | $10^{-5}$M | 0.17 | ND | ND | ND | 0.16 |
| pBM117 | $10^{-5}$M | 0.17 | ND | ND | ND | 9.21 |
| pBM113 | $10^{-5}$M | 0.11 | 4.38 | 42.93 | 290.09 | 712.80 |

*Ten units are equivalent to a specific activity of 9.2 pmoles 4-MU/μg protein/hour in this experiment.
**Incubation period in hours.
***ND = not done The results in Table 2 demonstrate the following:

1. There is no significant GUS activity intrinsic to the system either in the presence or absence of ABA (No DNA treatment).

2. There is no significant effect mediated by ABA on the 35S promoter-GUS construct (pBM117) implying that the effect is specific for promoter sequences normally modulated by ABA in vivo.

3. There is a time-dependent effect of ABA on the Em promoter-GUS construct (pBM113).

EXAMPLE 9

Effect of Phaseic Acid on Em Promoter

The protoplasts for this example are from the same source as that for EXAMPLE 7. Protoplasts were transformed with either calf thymus (CT) DNA, with pBM113 plasmid DNA or pBM117 plasmid DNA by the procedure described in the section entitled "Transformation of Protoplasts". CT DNA is non-specific DNA derived from calf thymus and is used as a negative control in protoplast transformation.

Protoplast suspensions containing $1 \times 10^6$ protoplasts were used. Protoplast suspensions receiving CT DNA were transformed by the addition of 25 μg of CT DNA and those being transformed with DNA from pBM117 received 5 μg plasmid DNA and 20 μg of CT DNA.

Protoplast suspensions to be transformed with DNA from plasmid pBM113 contained $2.0 \times 10^6$ protoplasts, 10.0 μg plasmid DNA and 15 μg CT DNA. After the transformation procedure, the suspensions transformed with CT DNA and DNA from pBM117 were each divided into two equal aliquots (0.5 $\times 10^6$ protoplasts each) and incubated in protoplast medium. One aliquot was without ABA while the other contained $10^{-4}$M ABA. The suspension transformed with DNA from pBM113 was divided into 3 aliquots (0.5 $\times 10^6$ protoplasts each) and similarly incubated in protoplast medium either without ABA, with $10^{-4}$M ABA or with $10^{-4}$M phaseic acid (PA).

After the incubation period (4 hours), the protoplasts in each culture were collected by centrifugation and stored at $-70°$ C. in GUS lysis buffer. All aliquots were later assayed for enzyme activity. The results are shown in Table 3.

TABLE 3

| Treatment | | | |
|---|---|---|---|
| Source of Input DNA | [ABA] | [PA]** | Specific Activity* (Units) |
| CT | 0 | 0 | 2.02 |
| CT | $10^{-4}$M | 0 | 1.81 |
| pBM117 | 0 | 0 | 10.00 |
| pMB117 | $10^{-4}$M | 0 | 9.20 |
| pBM113 | 0 | 0 | 8.24 |
| pBM113 | $10^{-4}$M | 0 | 31.51 |
| pBM113 | 0 | $10^{-4}$M | 8.36 |

*Ten units are equivalent to 2.18 pmoles 4-MU/μg protein/hour in this experiment.
**Phaseic Acid The results from Table 3 demonstrate that phaseic acid, a structural analog and the first breakdown product of ABA in vivo, does not induce expression of the Em promoter-GUS construct. This is consistent with previous results in which phaseic acid does not mediate the in vivo physiological effects attributed to ABA in wheat embryos, i.e., phaseic acid does not inhibit seed germination. Non-specific, non-plant DNA (CT) did not respond to ABA.

EXAMPLE 10

Equivalence of pBM113 and pBM113Kp

The source of protoplasts for this example is the same as that used in EXAMPLE 7. For this example, several cultures, each containing $2 \times 10^6$ protoplasts either received no DNA or were transformed, as described in EXAMPLE 7, with plasmid DNA (2 μg) of the plasmids pBM117, pBM113, pBM113Kp or pBM311. Those suspensions which did not receive DNA, or received either pBM117 DNA or pBM311 DNA were divided into 2 equal aliquots after the transformation protocol, placed in protoplast medium, and incubated for 18 hours ether in the presence of $10^{-4}$M ABA or without added ABA. Transformations with pBM113 and pBM113Kp were each done in duplicate and the duplicates were pooled.

The pooled duplicates were then split into four (4) equal aliquots. The transformed protoplasts were incubated for 18 hours in protoplast medium at 25° C. in the dark. The protoplast medium contained the concentration of ABA shown in the table below. The results of the GUS assay of these treatments are given in Table 4.

TABLE 4

| | Treatment | | |
|---|---|---|---|
| Sample | Source of Input DNA | [ABA] | Specific Activity* (Units) |
| (1) | NO DNA | 0 | 0.17 |
| (2) | NO DNA | $10^{-4}$M | 0.15 |
| (3) | pBM117 | 0 | 10.00 |
| (4) | pBM117 | $10^{-4}$M | 8.24 |
| (5) | pBM113 | 0 | 17.15 |
| (6) | pBM113 | $10^{-4}$M | 563.05 |
| (7) | pBM113 | $10^{-5}$M | 233.20 |
| (8) | pBM113 | $10^{-6}$M | 109.77 |
| (9) | pBM113Kp | 0 | 18.50 |
| (10) | pBM113Kp | $10^{-4}$M | 1170.09 |
| (11) | pBM113Kp | $10^{-5}$M | 403.70 |
| (12) | pBM113Kp | $10^{-6}$M | 130.61 |
| (13) | pBM311 | 0 | 0.21 |
| (14) | pBM311 | $10^{-4}$M | 0.45 |

*Ten units are equivalent to 6.59 pmoles 4-MU produced/μg protein/hour in this experiment.

The results represented in Table 4 demonstrate:

1. Expression of GUS activity from plasmids pBM113 and pBM113Kp is regulated by the presence of ABA (Treatment Samples 5 and 6; 9 and 10).

2. The induction of GUS expression from both plasmids, pBM113 and pBM113Kp, is not only regulated by ABA, but the level of expression is dependent on the concentration of ABA in the medium (Treatment Samples 6–8; 10–12).

3. The plasmid pBM113Kp, which contains only 652 bp of the Em promoter region, behaves similarly to the plasmid pBM113, which contains approximately 1850 bp of the Em promoter region (Treatment Samples 5–8; 9–12).

4. Plasmid pBM311, which contains only 652 bp of the Em promoter region linked to GUS in the wrong orientation (unoperably linked), did not significantly express GUS activity when treated with ABA (Treatment Samples 13–14). Furthermore, the low levels of activity seen with the same promoter fragment operably linked to GUS (pBM113Kp) when incubated without ABA, is totally abolished when pBM311 is used (compare Treatment Samples 9 and 13).

EXAMPLE 11

Response of a 254 bp Promoter Fragment to ABA

The source of protoplasts for this EXAMPLE is the same as that used in EXAMPLE 7. Transformations were performed using $2 \times 10^6$ protoplasts and 2 µg of plasmid DNA (except for the control samples which did not receive DNA). Each suspension of transformed protoplasts were split equally ($1 \times 10^6$ protoplasts) into protoplast medium either without ABA or with $10^{-4}$ M ABA and incubated at 25° C. in the dark for 18 hours. The protoplasts were then collected and assayed for GUS activity. The results are given in Table 5.

TABLE 5

| | Treatment | | |
|---|---|---|---|
| Sample | Source of Input DNA | [ABA] | Specific Activity* (Units) |
| (1) | NO DNA | 0 | 0.86 |
| (2) | pBM117 | 0 | 10.00 |
| (3) | pBM113Δ220.9 | 0 | 21.83 |
| (4) | pBM113Δ220.9 | $10^{-4}$ M | 282.90 |
| (5) | pBM113Δ220.10 | 0 | 21.29 |
| (6) | pBM113Δ220.10 | $10^{-4}$ M | 802.31 |
| (7) | pBM113Δ240.13 | 0 | 1.83 |
| (8) | pBM113Δ240.13 | $10^{-4}$ M | 4.3 |

*Ten units are equivalent to 1.86 pmoles 4-MU produced/µg protein/hour in this experiment.

The results of the above experiment demonstrate:

1. Plasmids containing fragments of the Em promoter to $-291$ bp (pBM113Δ220.10) and $-254$ bp (pBM113Δ220.9) 5' from the translation start codon (ATG) operably linked to GUS still retain the ability to be induced by ABA (Treatment Samples 3 and 4; 5 and 6).

2. A plasmid containing a fragment of the Em promoter to $-192$ bp (pBM113Δ240.13) 5' from the translation start codon (ATG) operably linked to GUS cannot be induced by ABA (Treatment Samples 7 and 8).

3. Deletion to $-192$ bp from the ATG not only prevents ABA enhancement of expression from the Em promoter region but also abolishes the low level of expression seen in the absence of ABA using longer Em promoter fragments (Compare Treatment Samples 7 with 3 and 5).

4. Plasmids pBM113Δ220.9 and pBM113Δ240.13 define a region of 62 bp in the Em promoter ($-192$ to $-254$) at least part of which is necessary for the ABA induction (ABA regulatory region).

EXAMPLES 12/13

Effect of two ABA analogs (Compounds C and D) on Em Promoter

The source of protoplasts for this EXAMPLE is the same as in EXAMPLE 7. The transformation was performed in duplicate using $50 \times 10^6$ protoplasts and 100 µg of plasmid DNA. The transformed protoplasts were split four ways and incubated in culture medium containing either ABA, Compound C, Compound D, or with no additions, at 25° C. in the dark for 18 hours. The protoplasts were then collected and assayed for GUS activity as described. The results are given in Table 6.

TABLE 6

| Sample | Source of Input DNA | Additions to Culture Medium | Specific Activity (pmoles 4-MU/µg protein/hour) |
|---|---|---|---|
| 1 | No DNA | — | 2.05 |
| 2 | pBM113Kp | — | 3.24 |
| 3 | pBM113Kp | ABA | 50.25 |
| 4 | pBM113Kp | Compound D | 38.89 |
| 5 | pBM113Kp | Compound C | 8.40 |

The results in Table 6 demonstrate the following:

1. Compounds C and D, both structural and functional analogs of ABA, induce expression of GUS activity from plasmid pBM113Kp at a concentration of $10^{-4}$ M.

2. Compounds D and ABA induce GUS activity approximately 20-fold over no additions, while Compound C had an approximate 4-fold stimulation.

3. These results and those of EXAMPLE 8 confirm that this transient expression system can rapidly and specifically determine if close structural and/or functional analogs of ABA possess gene-inducing activity, and can be used as a screen to identify analogs as potential inducers of gene expression.

EXAMPLE 14

The results from EXAMPLE 11 clearly demonstrate that at least part of the DNA sequences necessary for ABA-mediated regulation of gene expression reside in a 62 bp region between $-192$ and $-254$ bp from the ATG codon of the Em coding region (as defined by plasmids pBM113Δ240.13 and pBM113Δ220.9, respectively). Within this region is a sequence, 25 bp in length, which bears close homology (76%) to a sequence from the β-conglycinin gene of the dicot soybean. β-conglycinin expression is also developmentally regulated by ABA (see page 4). This region of homology is at the promoter proximal end of, and is completely contained within, the 62 bp region. The presence of this region of homology prompted the synthesis of the 56 bp oligo (see above). The introduction of the 56 bp oligo into a foreign promoter will cause expression from the foreign promoter to be influenced by ABA.

The protoplasts for this example are from the same source as that for EXAMPLE 7. Protoplasts were transformed with either no DNA, with pBM117 plasmid DNA, or with pBM167 plasmid DNA by the procedure described in the section entitled "Transformation of Protoplasts". The pBM167 series of plasmids is as described in EXAMPLE 5.

Protoplast suspensions containing $4 \times 10^6$ protoplasts were used and were transformed by the addition of either no DNA or by the addition of 4 µg plasmid DNA. After the transformation procedure, the suspensions were divided into two equal aliquots ($2 \times 10^6$ protoplasts each) and incubated in protoplast medium. One aliquot of each sample was incubated without ABA while the other was incubated with $10^{-4}$ M ABA. After the incubation period, the protoplasts in each culture were collected by centrifugation and lysed by addition of 0.5 ml GUS assay/lysis buffer. All aliquots were assayed for GUS enzyme activity and the results are shown in Table 7.

TABLE 7

| | Treatment | | Specific Activity |
|---|---|---|---|
| Sample | Source of Input DNA | [ABA] | (pmoles 4 MU/µg protein/hour) |
| 1 | No DNA | 0 | 1.02 |

TABLE 7-continued

| Sample | Treatment | | Specific Activity (pmoles 4 MU/μg protein/hour) |
|---|---|---|---|
| | Source of Input DNA | [ABA] | |
| 2 | No DNA | $10^{-4}$M | 1.02 |
| 3 | pBM152 | 0 | 1777.13 |
| 4 | pBM152 | $10^{-4}$M | 1730.42 |
| 5 | pBM167-11 | 0 | 1108.50 |
| 6 | pBM167-11 | $10^{-4}$M | 2081.18 |
| 7 | pBM167-4 | 0 | 104.39 |
| 8 | pBM167-4 | $10^{-4}$M | 560.51 |

The results in Table 7 demonstrate the following points:

1. There is no significant GUS activity intrinsic to the rice protoplast system, in the presence or absence of ABA (Treatment Samples 1 and 2).

2. There is no significant effect mediated by ABA on the 35S promoter-GUS construct, pBM152 (Treatment Samples 3 and 4). The 35S promoter is unresponsive to ABA.

3. There is a decrease of over 30% in GUS activity directed by the 35S promoter upon insertion of one copy of the 56 bp oligo into this promoter (Compare Treatment Samples 3 and 5). When two tandem copies of the 56 bp oligo are inserted into the 35S promoter, a decrease of over 90% in GUS activity is observed (Compare Treatment Samples 3 and 7). The reason for this decrease is not clear.

4. However, there is a significant increase in GUS activity over these levels when protoplasts containing plasmids with the 56 bp oligo inserted in the 35S promoter are treated with ABA: about two-fold with one copy of the 56 bp oligo (plasmid pBM167-11, and, over five-fold with two copies (plasmid pBM167-4). Compare Treatment Samples 5 with 6, and 7 with 8.)

These results clearly demonstrate that the 56 bp oligo contains ABA-regulatory sequences that confer ABA regulation to the normally ABA-unresponsive 35S promoter.

EXAMPLE 15

Expression of GUS activity in maturing seeds of transgenic tobacco

Binary plasmids containing the plasmids pBM1170 ($^{35}$S-GUS) and pBM1130 (Em-GUS) were introduced into the Gram-negative bacterium *Agrobacterium tumefaciens* by the method of triparental mating and subsequently introduced into tobacco tissue by the leaf disk transformation protocol. Transgenic tobacco plants were selected and grown as described earlier. At various times after flowering, seeds at different stages of maturation were collected and assayed for GUS activity. Detailed procedures are described in the section "Stable Transformation of Tobacco".

TABLE 8

| Sample | Promoter Construction | Stages of Seed Maturity | Specific Activity* (pmole 4 MU/min/ μg protein) |
|---|---|---|---|
| 1 | pBM1170 | Very Immature (white) | 1,037 |
| 2 | pBM1170 | Immature (tan) | 307 |
| 3 | pBM1170 | Mature (brown) | 269 |
| 4 | pBM1130 | Very Immature (white) | 2 |
| 5 | pBM1130 | Immature (tan) | 8 |

TABLE 8-continued

| Sample | Promoter Construction | Stages of Seed Maturity | Specific Activity* (pmole 4 MU/min/ μg protein) |
|---|---|---|---|
| 6 | pBM1130 | Mature (brown) | 29,000 |

*Each value is the average of 2 samples taken from the same capsule of a single transformed tobacco plant. Seeds from untransformed tobacco plants showed no GUS activity. Values represent activity over time zero in the enzyme assay.

The results of the above experiment demonstrate:

1. Tobacco plants transformed with plasmid pBM1170 (Samples 1–3) show similar levels of accumulated GUS activity in seeds at various stages of maturity; from the very immature (white seeds), the immature (tan seeds) and the dry mature seed (dark brown.) 35S is a constitutive promoter in higher plants and clearly shows its predicted activity throughout seed development.

2. Tobacco plants transformed with plasmid pBM1130 (Samples 4–6) show increasing amounts of accumulated GUS activity in seeds at later stages of maturation. This pattern of GUS accumulation in later stages of transgenic tobacco seeds is similar to increasing Em expression in normal wheat seeds indicating that the fragment of the Em promoter (650 bp) linked to GUS is being regulated in a manner predictable from its normal expression in wheat.

3. The Em promoter fragment from wheat (monocot) is recognized and regulated in a normal pattern in tobacco (dicot), presumably by the increasing endogenous levels of ABA occurring in late seed development.

EXAMPLE 16

Expression of GUS activity in transgenic tobacco seeds in response to ABA

Binary plasmids pBM1170 (35S-GUS), pBM1130 (Em-GUS) and pBM3110 (mE-GUS) were introduced into Agrobacterium and used to transform tobacco leaf disks by the methods outlined in EXAMPLE 15 and in the section Stable Transformation of Tobacco. Immature seeds (tan in color) were removed form the capsule as described in Stable Transformation of Tobacco and incubated for 24 hours on MX-medium with or without ABA.

TABLE 9

| Sample | Promoter Construction | [ABA] | Specific Activity* (pmole 4 MU/min/ μg protein) |
|---|---|---|---|
| 1 | pBM1170 | 0 | 29 |
| 2 | pBM1170 | $10^{-4}$M | 33 |
| 3 | pBM1130 | 0 | 50 |
| 4 | pBM1130 | $10^{-4}$M | 160 |
| 5 | pBM3110 | 0 | 0 |
| 6 | pBM3110 | $10^{-4}$M | 0 |

*Samples 1 and 2 each represent an average of 4 seed samples (immature seed-tan) taken from two capsules of a single transformant. Samples 3 and 4 each represent an average of 4 seed samples (immature seed-tan) taken from two capsules of another single transformant. Samples 5 and 6 represent an average of 2 seed samples (immature seed-tan) taken from one capsule of one transformant. Values represent values over time zero in the enzyme assay. Seeds from untransformed tobacco plants showed no GUS activity.

1. Tobacco plants transformed with plasmid pBM1170 (Samples 1 and 2) showed no stimulation of GUS activity when immature seeds were incubated with $10^{-4}$M ABA. These results in stable transformants are identical to the results obtained with the same constructs in the transient system (see EXAMPLE 10, Table 4).

2. Tobacco plants transformed with plasmid pBM1130 (Samples 3 and 4) showed approximately a 3-fold increase of GUS activity when immature seeds were incubated in $10^{-4}$M ABA. When the promoter is reversed (Samples 5 and 6) no GUS activity is expressed. These results are identical to the results obtained with the same constructs in the transient system (see EXAMPLE 10, Table 4).

3. Results 1) and 2) demonstrate the ability of the transient assay to accurately predict expression of GUS in transgenic plants.

4. The EM promoter fragment from wheat (monocot) is recognized and regulated by ABA in transgenic tobacco (dicot) in the same manner as in wheat, i.e., isolated immature wheat embryos when treated with ABA express the Em gene.

EXAMPLE 17

Development of Drought Tolerance in Plants

The Em protein of wheat has been implicated in protection of the embryo during seed desiccation (McCubbin et al., *Can. J. Biochem. Cell Biol.*, 63:803–811 (1985) and Litts et al., *Nucl. Acids Res.* 15:3607–3618 (1987)). Normally during the life cycle of the wheat plant, Em is accumulated only in the embryo of seeds. It will be valuable to express this protein, with its natural ability to bind water, not just in seeds but in whole plants or specific tissue(s) that are experiencing unpredictable drought or water stress. Such expression and accumulation of the Em protein will allow the plant or its affected parts to retain water.

We will use the information gained in the construction of this invention to protect plants under drought conditions. A general response of plants to water stress or drought is to accumulate large amounts of ABA in affected tissue (e.g., Guerrero and Mullet, *Plant Physiol.* 80:588–591 (1986)). The ABA regulatory region of the Em promoter will be used to over-produce the Em protein under conditions of water stress, resulting in the plant becoming tolerant to these adverse conditions.

In Example 14, we described a "56 bp oligo", containing a 50 bp region of the wheat Em promoter, that was sufficient for ABA regulation of GUS. We have operably linked this inducible ABA regulatory region of the Em promoter with the constitutive 35S promoter of CaMV by synthesizing the 56 bp oligo such that it can be inserted into the EcoRV site present in the 35S promoter. The 35S promoter will provide the polymerase binding sequences necessary for transcription that have been removed from the ABA regulatory fragment. This chimeric promoter will then be operably linked to the coding region of Em. Such a construct, when stably transformed into plants, will direct the low level expression of the Em protein constitutively throughout the plant. However, when endogenous levels of ABA increase under drought conditions, an over-production of the Em protein will result due to the presence of the ABA regulatory sequence, thereby protecting the tissue experiencing the water stress.

What is claimed is:

1. A nucleic acid promoter fragment comprising the 5' flanking promoter region of the Em structural gene of wheat which is inducible by at least one of the compounds selected from the group consisting of ABA, Compound C, Compound D, Compound E, and Compound F.

2. A nucleic acid promoter fragment of claim 1 wherein said promoter fragment comprises about 1850 base pairs.

3. A DNA construct comprising the 5' flanking promoter region of the Em structural gene of wheat operably linked to a nucleotide sequence for a selected gene product and capable of transforming a plant cell or protoplast such that said promoter region is responsive to at least one of the compounds selected from the group consisting of ABA, Compound C, Compound D, Compound E, and Compound F to control the expression of said nucleotide sequence for a selected gene product in said plant cell or protoplast.

4. A nucleic acid promoter fragment of claim 1 comprising the nucleotide sequence of 1328 base pairs corresponding to base pairs 1 to 1328 in FIG. 3.

5. A nucleic acid promoter fragment of claim 1 comprising the nucleotide sequence of 640 base pairs corresponding to base pairs 689 to 1328 in FIG. 3.

6. A nucleic acid promoter fragment of claim 1 comprising the nucleotide sequence of 254 base pairs corresponding to base pairs 1075 to 1328 in FIG. 3.

7. A nucleic acid promoter fragment of claim 1 comprising the nucleotide sequence of 50 base pairs corresponding to base pairs 1091–1140 in FIG. 3.

8. A recombinant DNA construct capable of transforming a plant cell or protoplast comprising a nucleic acid promoter fragment of claims 1, 2, 4, 5, 6 or 7 and a DNA sequence for a selected gene product operably linked to said promoter fragment such that upon exposure of a transformed plant cell or protoplast to at least one of the compounds selected from the group consisting of ABA, Compound C, Compound D, Compound E, and Compound F said DNA sequence for a selected gene product is expressed.

9. A recombinant DNA construct of claim 8 wherein said selected gene product is the sequence for β-glucuronidase.

10. A recombinant DNA construct of claim 8 wherein said plant cell or protoplast is a rice plant cell or protoplast.

11. A substantially pure preparation of the Em nucleic acid promoter fragment of wheat which is inducible by at least one of the compounds selected from the group consisting of ABA, Compound C, Compound D, Compound E, and Compound F.

* * * * *